United States Patent
Evers et al.

(10) Patent No.: US 10,473,670 B2
(45) Date of Patent: Nov. 12, 2019

(54) METHOD OF PREDICTING OBESITY COMPRISING MEASURING NEUROTENSIN

(71) Applicants: University of Kentucky Research Foundation, Lexington, KY (US); University of Massachusetts, Worcester, MA (US); Lund University, Malmö (SE)

(72) Inventors: B. Mark Evers, Lexington, KY (US); Jing Li, Lexington, KY (US); Paul Dobner, Worcester, MA (US); Olle Melander, Malmö (SE)

(73) Assignees: University of Kentucky Research Foundation, Lexington, KY (US); University of Massachusetts, Boston, MA (US)

(*) Notice: Subject to any disclaimer, the term of this patent is extended or adjusted under 35 U.S.C. 154(b) by 0 days.

(21) Appl. No.: 15/443,266

(22) Filed: Feb. 27, 2017

(65) Prior Publication Data
US 2017/0248610 A1 Aug. 31, 2017

Related U.S. Application Data

(60) Provisional application No. 62/299,688, filed on Feb. 25, 2016.

(51) Int. Cl.
| | |
|---|---|
| *G01N 33/68* | (2006.01) |
| *A61K 38/00* | (2006.01) |
| *C12N 15/113* | (2010.01) |
| *C12Q 1/6883* | (2018.01) |

(52) U.S. Cl.
CPC ......... *G01N 33/6893* (2013.01); *A61K 38/00* (2013.01); *C12N 15/113* (2013.01); *C12Q 1/6883* (2013.01); *C12N 2310/14* (2013.01); *C12Q 2600/158* (2013.01); *G01N 2333/912* (2013.01); *G01N 2440/14* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 8,476,221 B2 | 7/2013 | Ghatnekar et al. | |
| 2005/0233393 A1 | 10/2005 | Edwards | |
| 2008/0065136 A1 | 3/2008 | Young | |
| 2010/0256055 A1 | 10/2010 | Castaigne | |
| 2011/0046956 A1 | 2/2011 | Auburn et al. | |
| 2013/0323760 A1 | 12/2013 | Kang | |

FOREIGN PATENT DOCUMENTS

| | | | | |
|---|---|---|---|---|
| EP | 1157695 | * | 11/2001 | .......... A61K 31/505 |
| WO | 2008008357 A1 | | 1/2008 | |
| WO | 2013132090 A1 | | 9/2013 | |
| WO | WO2016/066862 | * | 5/2016 | |

OTHER PUBLICATIONS

Martin et al., JBC, 2006; 281: 18933-18941 (Year: 2006).*
Bergmann; EP15156995; Certified Priority Document of PCT/EP2016/054106 (WO2016/066862): 31 pages total (Year: 2015).*
Li et al., Nature, 2016; 533: 411; doi:10.1038/nature17662 (Year: 2016).*
Pirollo et al., Cancer Res. 2008; 68(5): 1247-1250 (Year: 2008).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
Piche-Nicholas et al., MAbs. 2018; 10: 81-94. doi: 10.1080/19420862.2017.1389355 (Year: 2018).*
Sarah Crunkhorn, Nature Reviews Drug Discovery; Published online Jun. 17, 2016; doi:10.1038/nrd.2016.121 (Year: 2016).*
Armstrong, M. J., Parker, M. C., Ferris, C. F. & Leeman, S. E. Neurotensin stimulates [3H]oleic acid translocation across rat small intestine. Am J Physiol 251, G823-829 (1986).
Birse, R. T. et al. High-fat-diet-induced obesity and heart dysfunction are regulated by the TOR pathway in *Drosophila*. Cell Metab 12, 533-544 (2010).
Boules, M. et al. A novel neurotensin peptide analog given extracranially decreases food intake and weight in rodents. Brain Res 865, 35-44 (2000).
Cooke, J. H. et al. Peripheral and central administration of xenin and neurotensin suppress food intake in rodents. Obesity (Silver Spring) 17, 1135-1143 (2009).
Dobner, P. R., Fadel, J., Deitemeyer, N., Carraway, R. E. & Deutch, A. Y. Neurotensindeficient mice show altered responses to antipsychotic drugs. Proc Natl Acad Sci U S A 98, 8048-8053 (2001).
Drucker DJ. The role of gut hormones in glucose homeostasis. J Clin Invest 117:24-32, 2007. PMCID:1716213.
Ernst, A., Hellmich, S. & Bergmann, A. Proneurotensin 1-117, a stable neurotensin precursor fragment identified in human circulation. Peptides 27, 1787-1793 (2006).
Evers, B. M. Neurotensin and growth of normal and neoplastic tissues. Peptides 27, 2424-2433 (2006).
Fan, T. W., Lane, A. N., Higashi, R. M. & Yan, J. Stable isotope resolved metabolomics of lung cancer in a SCID mouse model. Metabolomics 7, 257-269 (2011).

(Continued)

*Primary Examiner* — Christina M Borgeest
(74) *Attorney, Agent, or Firm* — Stites & Harbison PLLC; Mandy Wilson Decker

(57) ABSTRACT

The presently disclosed subject matter relates to a method for predicting increased risk of obesity on a non-obese subject. More particularly, the presently disclosed subject matter relates to a method of predicting increased risk of obesity in a non-obese subject by determining a level of neurotensin expression in a biological sample from the subject and comparing the level of neurotensin expression in the sample with a control level. The presently disclosed subject matter further relates to a method of preventing and/or treating obesity in a subject in need thereof by administering to the subject an effective amount of an agent that inhibits neurotensin.

17 Claims, 19 Drawing Sheets

Specification includes a Sequence Listing.

(56) References Cited

OTHER PUBLICATIONS

Ferris, C. F., Hammer, R. A. & Leeman, S. E. Elevation of plasma neurotensin during lipid perfusion of rat small intestine. Peptides 2 Suppl 2, 263-266 (1981).
Gully, D., et al., Biochemical and pharmacological activities of SR 142948A, a new potent neurotensin receptor antagonist. The Journal of Pharmacology and Experimental Therapeutics, 280:802-812 (1997).
Gully, D., et al., Biochemican and pharmacological profild of a potent and selective nonpeptide antagonist of the neurotensin receptor Proc. Natl. Acad. Sci. USA, vol. 90, pp. 65-69, (1993).
Hardie, D. G. AMPK: positive and negative regulation, and its role in whole-body energy homeostasis. Curr Opin Cell Biol 33C, 1-7 (2014).
Kopelman, P. G. Obesity as a medical problem. Nature 404, 635-643 (2000).
Li, J. et al. Cyclic adenosine 5'-monophosphate-stimulated neurotensin secretion is mediated through Rap1 downstream of both Epac and protein kinase A signaling pathways. Mol Endocrinol 21, 159-171 (2007).
Li, J. et al. mTORC1 inhibition increases neurotensin secretion and gene expression through activation of the MEK/ERK/c-Jun pathway in the human endocrine cell line BON. Am J Physiol Cell Physiol 301, C213-226 (2011).
Li, J. et al. PI3K p110alpha/Akt signaling negatively regulates secretion of the intestinal peptide neurotensin through interference of granule transport. Mol Endocrinol 26, 1380-1393 (2012).
Li, J. Chen, L. A., Townsend, C. M., Jr. & Evers, B. M. PKD1, PKD2, and their substrate Kidins220 regulate neurotensin secretion in the BON human endocrine cell line. J Biol Chem 283, 2614-2621 (2008).
Lim, C. T., Kola, B. & Korbonits, M. AMPK as a mediator of hormonal signalling. J Mol Endocrinol 44, 87-97 (2010).
Little TJ, Horowitz M and Feinle-Bisset C. Modulation by high-fat diets of gastrointestinal function and hormones associated with the regulation of energy intake: implications for the pathophysiology of obesity. Am J Clin Nutr 86:531-41, 2007.
Melander, O. et al. Plasma proneurotensin and incidence of diabetes, cardiovascular disease, breast cancer, and mortality. JAMA 308, 1469-1475 (2012).
Ogden, C. L., Yanovski, S. Z., Carroll, M. D. & Flegal, K. M. The epidemiology of obesity. Gastroenterology 132, 2087-2102 (2007).
Piliponsky, A. M. et al. Neurotensin increases mortality and mast cells reduce neurotensin levels in a mouse model of sepsis. Nat Med 14, 392-398 (2008).
Sahu, A. Carraway, R. E. & Wang, Y. P. Evidence that neurotensin mediates the central effect of leptin on food intake in rat. Brain Res 888, 343-347 (2001).
Stenesen, D. et al. Adenosine nucleotide biosynthesis and AMPK regulate adult life span and mediate the longevity benefit of caloric restriction in flies. Cell Metab 17, 101-112 (2013).
Vincent, J. P., Mazella, J. & Kitabgi, P. Neurotensin and neurotensin receptors. Trends Pharmacol Sci 20, 302-309 (1999).
Service et al., Neurotensin in diabetes and obesity, 14 Regul. Pept. 85 (1986).
Williams et al., Reduced hypothalamic neurotensin concentrations in the genetically obese diabetic (ob/ob) mouse: possible relationship to obesity, 40 Metabolism 1112 (1991).

* cited by examiner

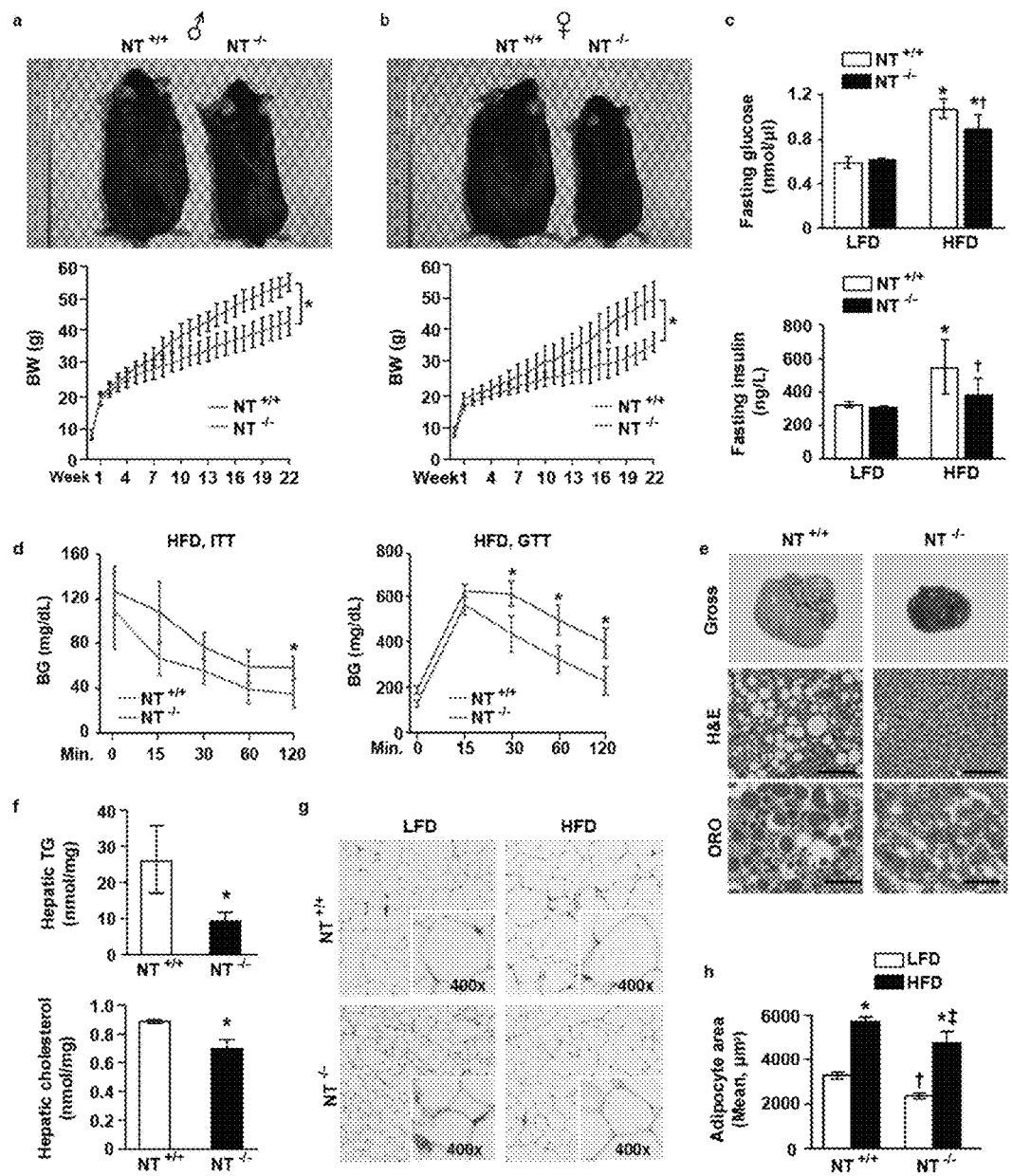
Figures 1A-H

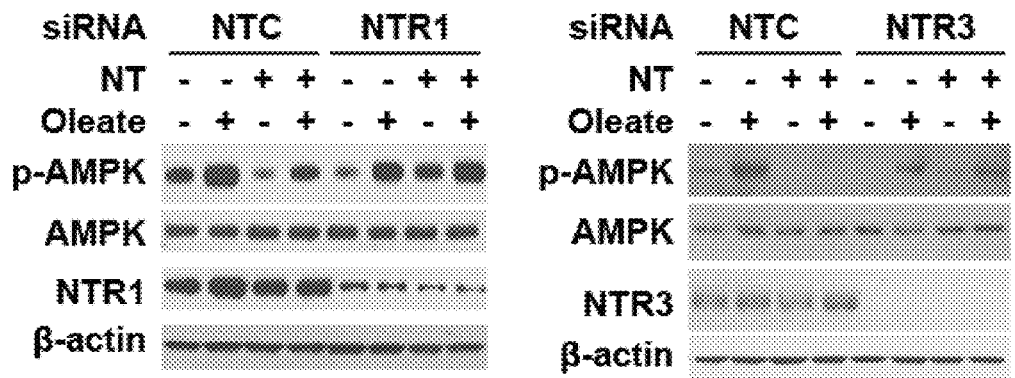
FIGURE 2I
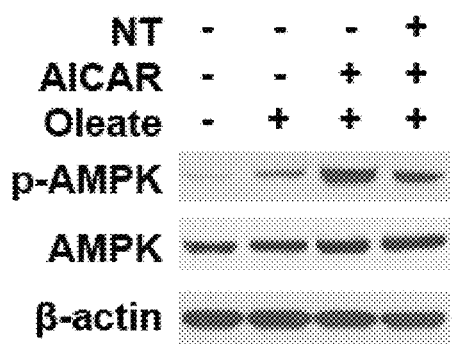
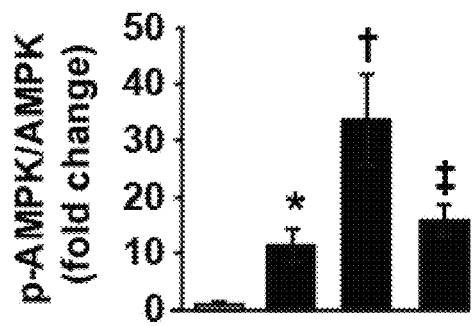
FIGURE 2J
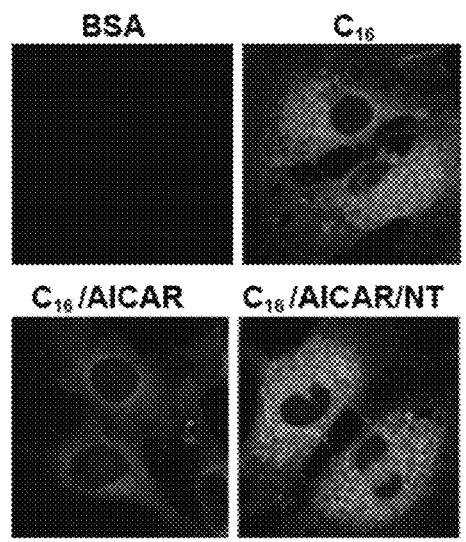
FIGURE 2K

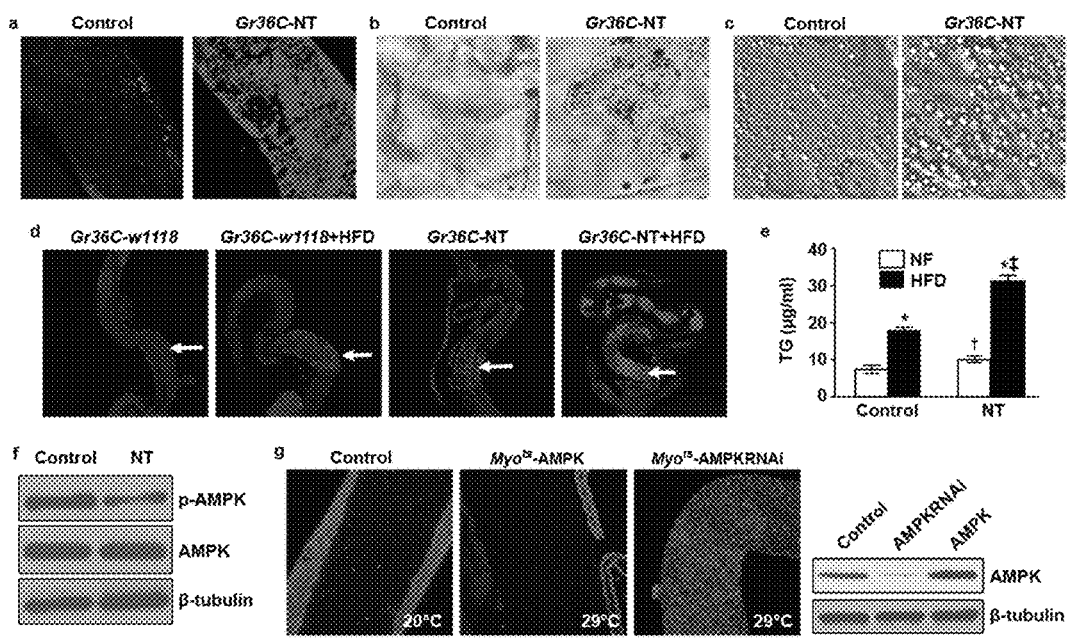
Figures 3A-G

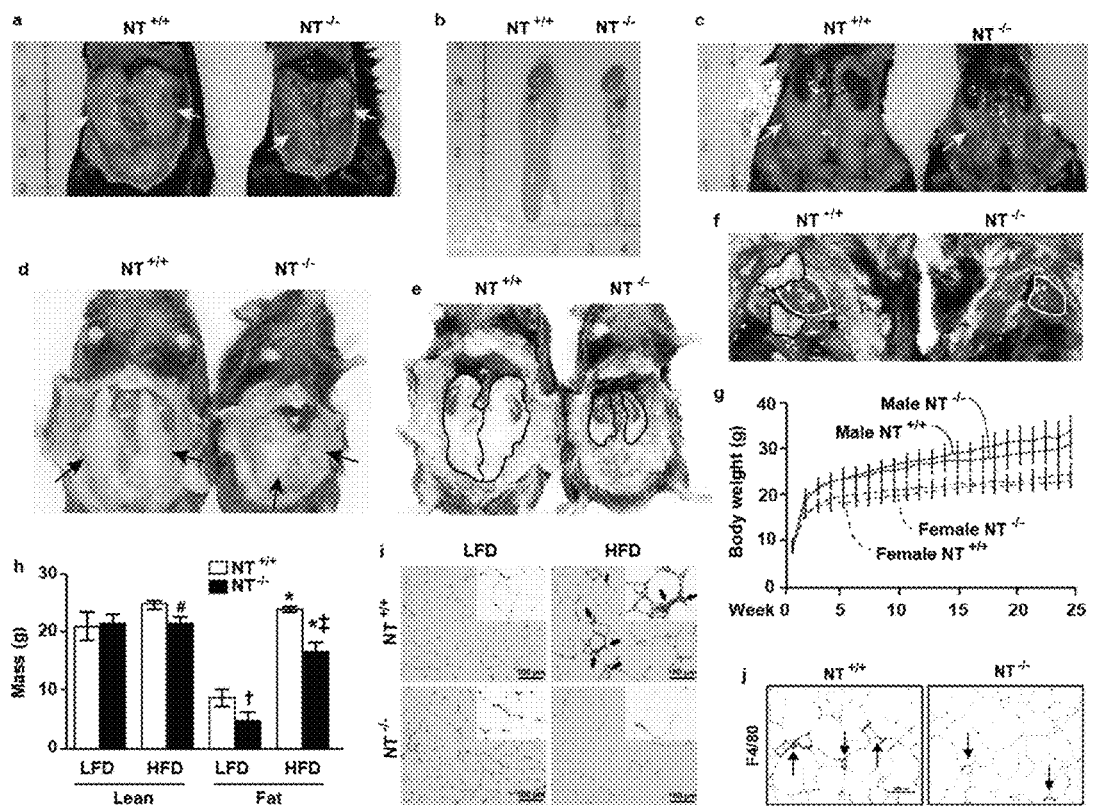
Figures 4A-J

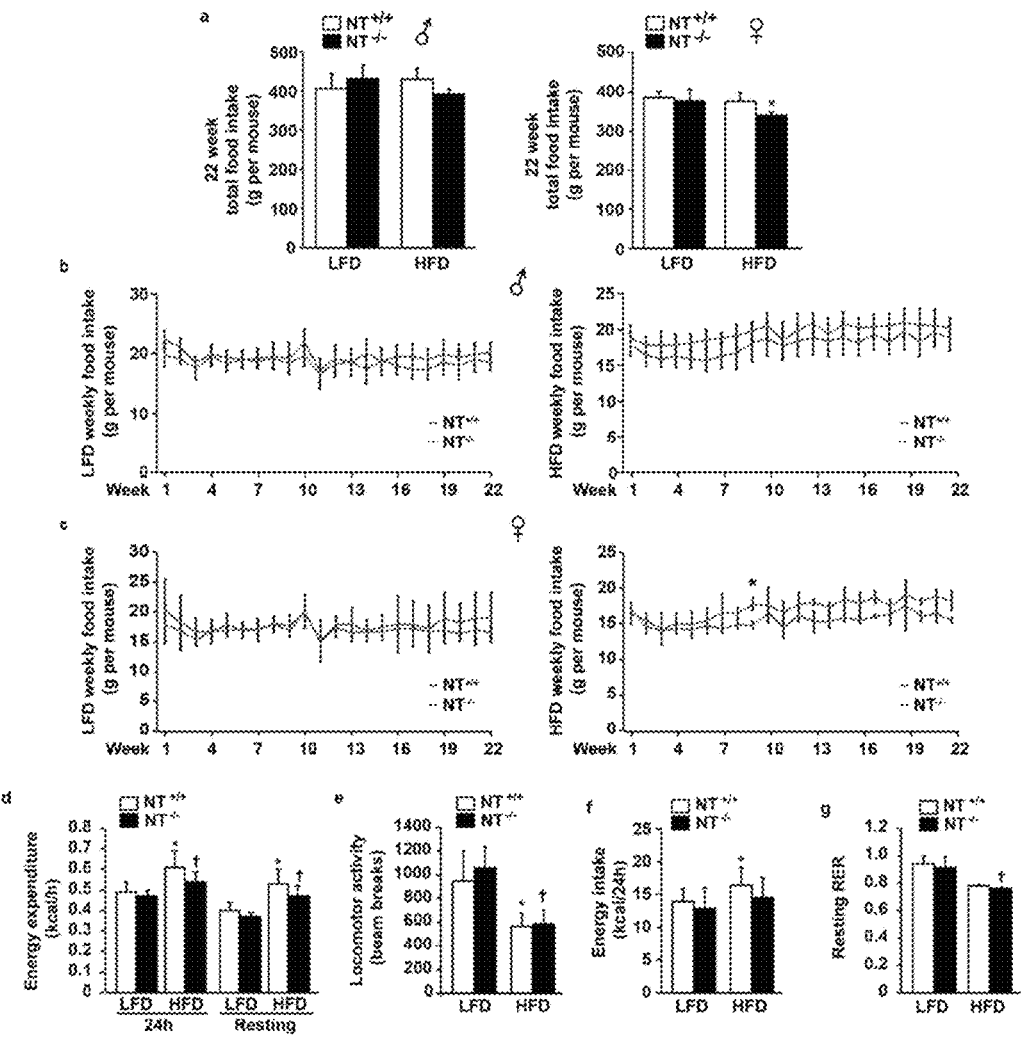
Figures 5A-G

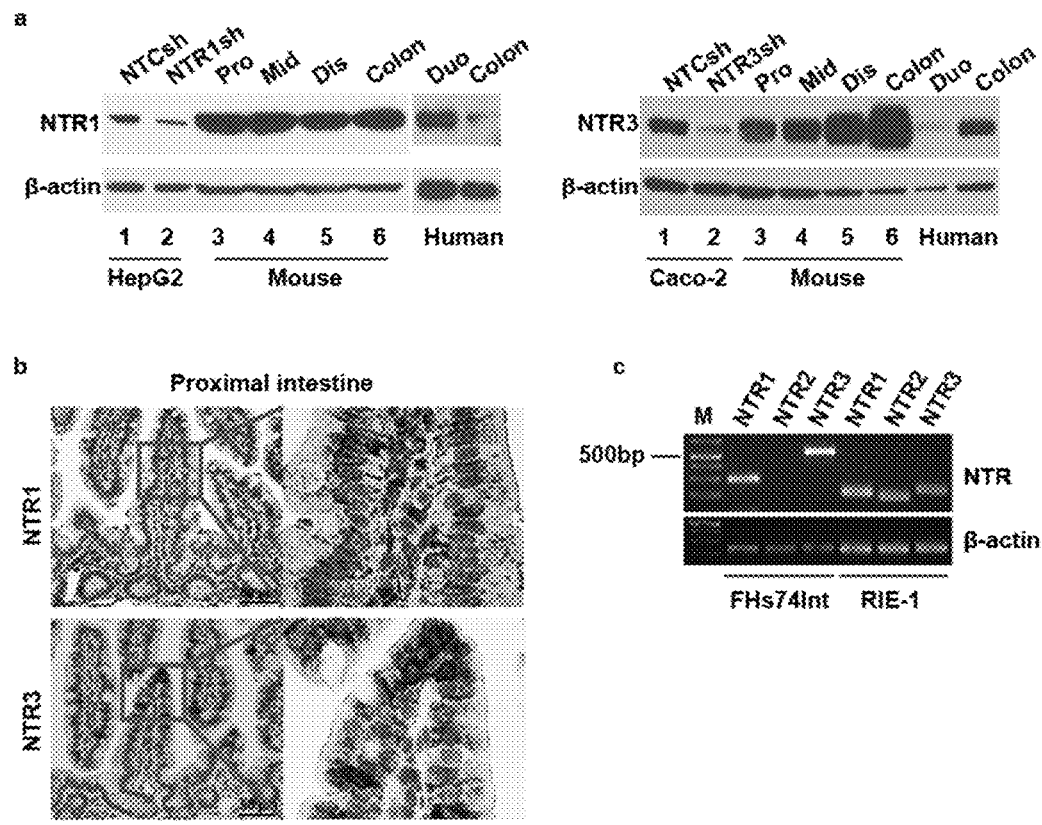
Figures 6A-C

Extended Data Fig. 8

```
Mouse NTR1   SGNSSESILEPNSNLDVNTDIYSKVLVTAVYLALFVVGTVGNSVTAFTLARKKSLQSLQS
             +GN S  +  P  L +      + VT VY  +F+ G VGN   T   +  +  +S+ +
Fly CG9918   AGNMSHDLGPPRDPLAI------VIPVTVVYSLIFITGVVGNISTCIVIKKNRSMHT---

Identities: 32.1%   TVHYHLGSLALSDLLILLLAMPVELYNFIWHHPWAFGDAGCRGYYFLRDACTYATALNV
Positives: 50.5%     +Y+L SLA+SD L+LL  +P E+ ++IW  +P+ FG+  C G    L  +    AT L +
                    ATNYYLFSLAISDFLLLLSGVPQEV-SYIWSKYPYVFGEYICIGRGLLAETSANATVLTI ASLSVERYLAICHPFKAKTLMSRSRTKKFISAIWLASALLAVPMLFTMGLQNRSADGQHP
                     +  +VERY+AICHPF  +  +    SR   + I  +W+ +  +  A+P       G+++ S  G
                    TAFTVERYIAICHPFLGQAMSKLSRAIRIIVLVWIMAIVTAIPQAAQFGIEHYS--GVEQ GGLVCTPTVDTATVKVVIQVNTFMSFLFPMLIISILNTVIANKL--TVMVHQAAEQGR--
                     G+V           VK    Q++TF+  FL PM II +L  +I    L  +  +V   A    R
                    CGIV------RVIVKHSFQLSTFIFFLAPMSIILVLYLLIGVHLYRSTLVEGPASVARRQ ----------------GVCTVGTHNS----------LEHSTFNMSIEPGRVQ--ALRHGVL
                                    G  T + N            +   S  +S   GR+     R +
                    QLKSVPSDTILYRYGGSGTAMSFNGGGSGAGTAGLMGGSGAQLSSVRGRLNHYGTRRVLR VLRAVVIAFVVCWLPYHVRRLMFCYISDEQWTTFLFDFYHYFYML----TNALFYVSSAI
                    +L AVV+ F +CW P+H +RL+  Y           L D + + Y +     + L+Y+S+ I
                    MLVAVVVCFFLCWAPFHAQRLIAIXAPARGAK--LRDQHEFVYTVMTYVSGVLYYLSTCI NPILYNLVSANFRQVFLSTL      384
                    NP+LYN++S  FR+  F  +  L
                    NPLLYNIMSHKFREAFKAVL      362
```

Figure 10E

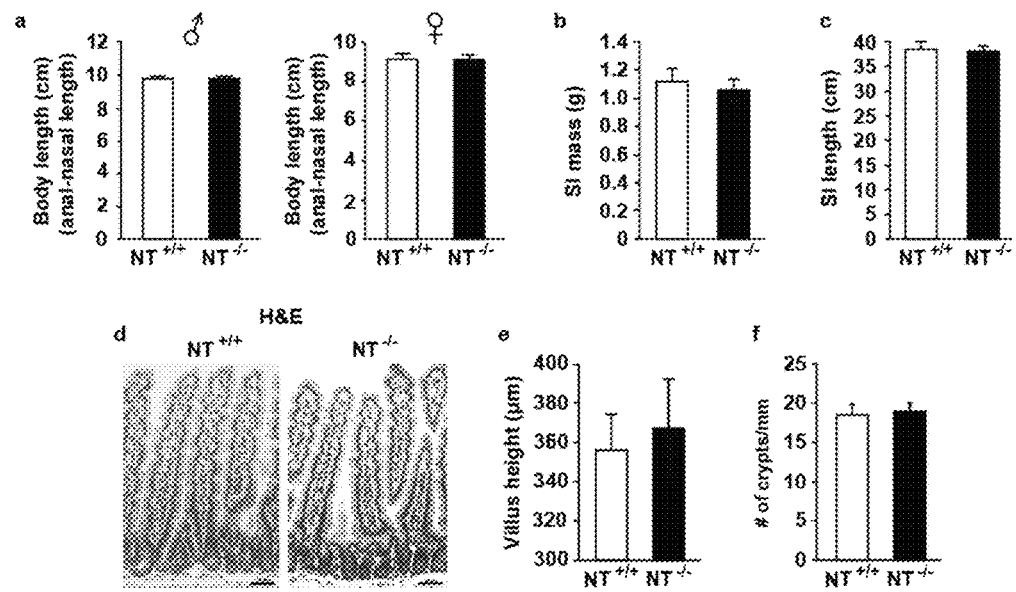
Figures 11A-F
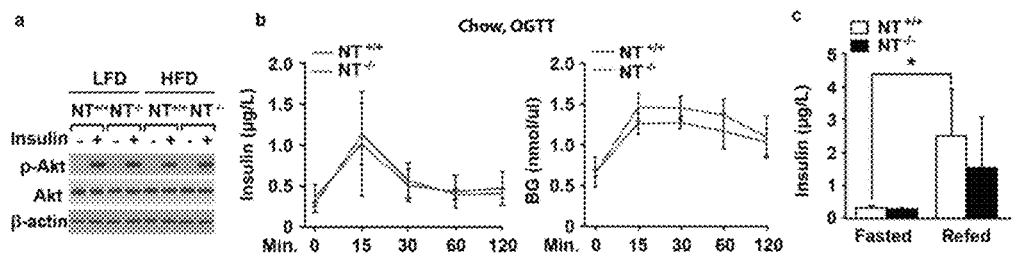
Figures 12A-C
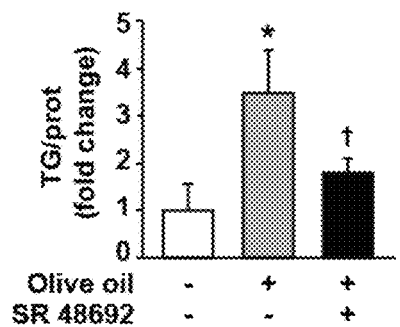
FIGURE 13A

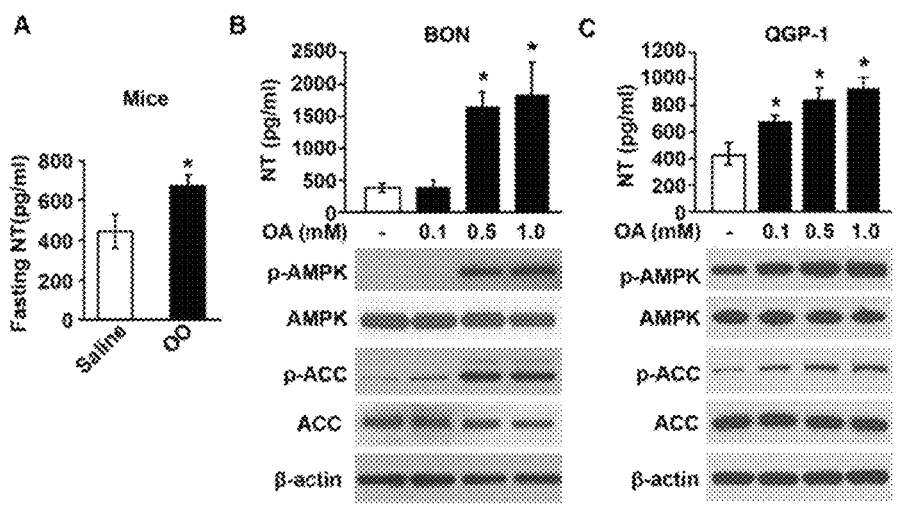
Figures 14A-C
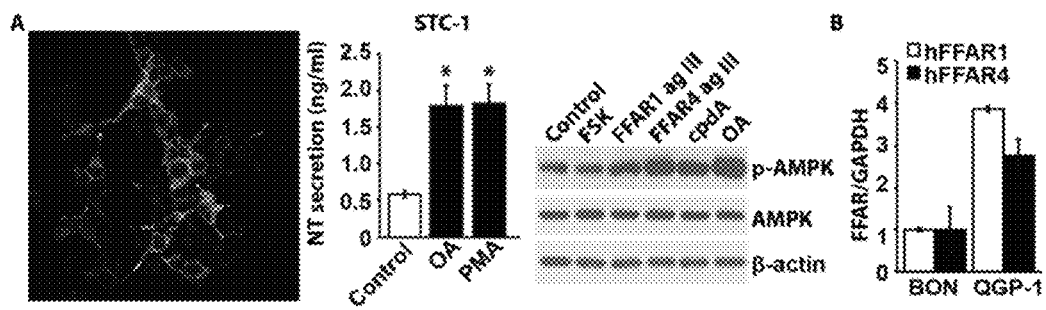
Figures 15A-B
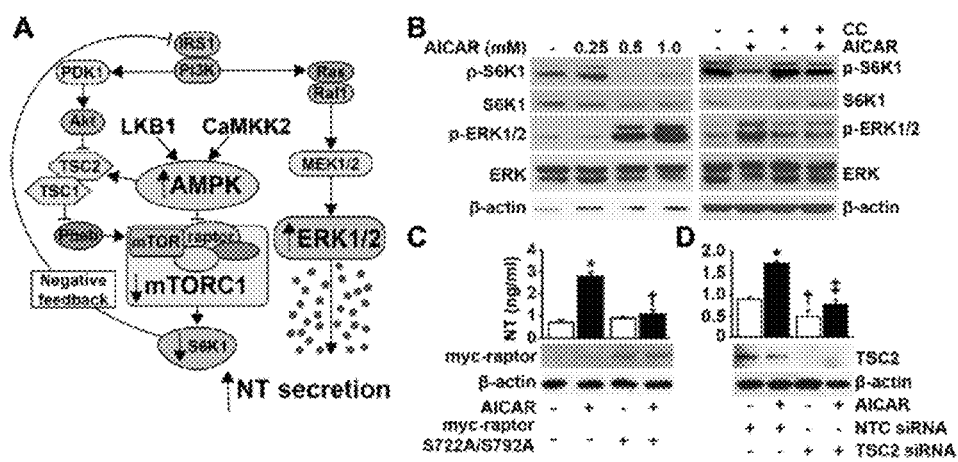
Figures 16A-D

SEQUENCE LISTING

<160> NUMBER OF SEQ ID NOS: 26

<210> SEQ ID NO 1

<211> LENGTH: 345
<212> TYPE: PRT
<213> ORGANISM: Mus musculus

<400> SEQUENCE: 1

Ser Gly Asn Ser Ser Glu Ser Ile Leu Glu Pro Asn Ser Asn Leu Asp
1               5                   10                  15

Val Asn Thr Asp Ile Tyr Ser Lys Val Leu Val Thr Ala Val Tyr Leu
            20                  25                  30

Ala Leu Phe Val Val Gly Thr Gly Asn Ser Val Thr Ala Phe Thr
        35                  40                  45

Leu Ala Arg Lys Lys Ser Leu Gln Ser Leu Gln Ser Thr Val His Tyr
    50                  55                  60

His Leu Gly Ser Leu Ala Leu Ser Asp Leu Leu Ile Leu Leu Leu Ala
65                  70                  75                  80

Met Pro Val Glu Leu Tyr Asn Phe Ile Trp Val His His Pro Trp Ala
                85                  90                  95

Phe Gly Asp Ala Gly Cys Arg Gly Tyr Tyr Phe Leu Arg Asp Ala Cys
            100                 105                 110

Thr Tyr Ala Thr Ala Leu Asn Val Ala Ser Leu Ser Val Glu Arg Tyr
        115                 120                 125

Leu Ala Ile Cys His Pro Phe Lys Ala Arg Thr Leu Met Ser Arg Ser
    130                 135                 140

Arg Thr Lys Lys Phe Ile Ser Ala Ile Trp Leu Ala Ser Ala Leu Leu
145                 150                 155                 160

Ala Val Pro Met Leu Phe Thr Met Gly Leu Gln Asn Arg Ser Ala Asp
                165                 170                 175

Gly Gln His Pro Gly Gly Leu Val Cys Thr Pro Thr Val Asp Thr Ala
            180                 185                 190

Thr Val Lys Val Val Ile Gln Val Asn Thr Phe Met Ser Phe Leu Phe
        195                 200                 205

Pro Met Leu Ile Ile Ser Ile Leu Asn Thr Val Ile Ala Asn Lys Leu
    210                 215                 220

Thr Val Met Val His Gln Ala Ala Glu Gln Gly Arg Gly Val Cys Thr
225                 230                 235                 240

Val Gly Thr His Asn Ser Leu Glu His Ser Thr Phe Asn Met Ser Ile
                245                 250                 255

Glu Pro Gly Arg Val Gln Ala Leu Arg His Gly Val Leu Val Leu Arg
            260                 265                 270

Ala Val Val Ile Ala Phe Val Val Cys Trp Leu Pro Tyr His Val Arg
        275                 280                 285

Arg Leu Met Phe Cys Tyr Ile Ser Asp Glu Gln Trp Thr Thr Phe Leu
    290                 295                 300

Phe Asp Phe Tyr His Tyr Phe Tyr Met Leu Thr Asn Ala Leu Phe Tyr
305                 310                 315                 320

Val Ser Ser Ala Ile Asn Pro Ile Leu Tyr Asn Leu Val Ser Ala Asn
                325                 330                 335

Phe Arg Gln Val Phe Leu Ser Thr Leu
            340                 345

<210> SEQ ID NO 2
<211> LENGTH: 360
<212> TYPE: PRT
<213> ORGANISM: Drosophila melanogaster

<400> SEQUENCE: 2

```
Ala Gly Asn Met Ser His Asp Leu Gly Pro Pro Arg Asp Pro Leu Ala
1               5                   10                  15

Ile Val Ile Pro Val Thr Val Val Tyr Ser Leu Ile Phe Ile Thr Gly
            20                  25                  30

Val Val Gly Asn Ile Ser Thr Cys Ile Val Ile Lys Lys Asn Arg Ser
        35                  40                  45

Met His Thr Ala Thr Asn Tyr Tyr Leu Phe Ser Leu Ala Ile Ser Asp
50                  55                  60

Phe Leu Leu Leu Leu Ser Gly Val Pro Gln Glu Val Ser Tyr Ile Trp
65                  70                  75                  80

Ser Lys Tyr Pro Tyr Val Phe Gly Glu Tyr Ile Cys Ile Gly Arg Gly
            85                  90                  95

Leu Leu Ala Glu Thr Ser Ala Asn Ala Thr Val Leu Thr Ile Thr Ala
        100                 105                 110

Phe Thr Val Glu Arg Tyr Ile Ala Ile Cys His Pro Phe Leu Gly Gln
        115                 120                 125

Ala Met Ser Lys Leu Ser Arg Ala Arg Ile Ile Val Leu Val Trp
130                 135                 140

Ile Met Ala Ile Val Thr Ala Ile Pro Gln Ala Ala Gln Phe Gly Ile
145                 150                 155                 160

Glu His Tyr Ser Gly Val Glu Gln Cys Gly Ile Val Arg Val Ile Val
            165                 170                 175

Lys His Ser Phe Gln Leu Ser Thr Phe Ile Phe Leu Ala Pro Met
        180                 185                 190

Ser Ile Ile Leu Val Leu Tyr Leu Leu Ile Gly Val His Leu Tyr Arg
        195                 200                 205

Ser Thr Leu Val Glu Gly Pro Ala Ser Val Ala Arg Arg Gln Gln Leu
        210                 215                 220

Lys Ser Val Pro Ser Asp Thr Ile Leu Tyr Arg Tyr Gly Gly Ser Gly
225                 230                 235                 240

Thr Ala Met Ser Phe Asn Gly Gly Ser Gly Ala Gly Thr Ala Gly
            245                 250                 255

Leu Met Gly Gly Ser Gly Ala Gln Leu Ser Ser Val Arg Gly Arg Leu
        260                 265                 270

Asn His Tyr Gly Thr Arg Arg Val Leu Arg Met Leu Val Ala Val Val
        275                 280                 285

Val Cys Phe Phe Leu Cys Trp Ala Pro Phe His Ala Gln Arg Leu Ile
        290                 295                 300

Ala Ile Tyr Ala Pro Ala Arg Gly Ala Lys Leu Arg Asp Gln His Glu
305                 310                 315                 320

Phe Val Tyr Thr Val Met Thr Tyr Val Ser Gly Val Leu Tyr Tyr Leu
            325                 330                 335

Ser Thr Cys Ile Asn Pro Leu Leu Tyr Asn Ile Met Ser His Lys Phe
            340                 345                 350

Arg Glu Ala Phe Lys Ala Val Leu
            355                 360
```

<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3
tcatcgcctt tgtggtctgc t                                              21

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
tggttgctgg acacgctgtc g                                              21

<210> SEQ ID NO 5
<211> LENGTH: 21
<212> TYPE: DNA
<213> ORGANISM: Artificial
<220> FEATURE:
<223> OTHER INFORMATION: PCR primer

<400> SEQUENCE: 5
gtctcctcag cttcatcgta t                                              21

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
tccccaaagc ctgaagctgt a                                              21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
agaatggtcg agactatgtt g                                              21

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
aagagctatt ccaagaggtc c                                              21

<210> SEQ ID NO 9
<211> LENGTH: 20
<212> TYPE: DNA
<213> ORGANISM: Artificial
<220> FEATURE:
<223> OTHER INFORMATION: PCR primer

<400> SEQUENCE: 9
gagaagcccc caaaattctc                                                20

<210> SEQ ID NO 10
<211> LENGTH: 20
<212> TYPE: DNA

```
<213> ORGANISM: Artificial
<220> FEATURE:
<223> OTHER INFORMATION: PCR primer

<400> SEQUENCE: 10
caaggaccca gtgcaggtat                                           20

<210> SEQ ID NO 11
<211> LENGTH: 20
<212> TYPE: DNA
<213> ORGANISM: Artificial
<220> FEATURE:
<223> OTHER INFORMATION: PCR primer

<400> SEQUENCE: 11
actcgctcat cttcgcattt                                           20

<210> SEQ ID NO 12
<211> LENGTH: 20
<212> TYPE: DNA
<213> ORGANISM: Artificial
<220> FEATURE:
<223> OTHER INFORMATION: PCR primer

<400> SEQUENCE: 12
tgggaccaca cgaagttgta                                           20

<210> SEQ ID NO 13
<211> LENGTH: 20
<212> TYPE: DNA
<213> ORGANISM: Artificial
<220> FEATURE:
<223> OTHER INFORMATION: PCR primer

<400> SEQUENCE: 13
tttcaagctg tgctttgtgg                                           20

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
agttctctga acgggagcaa                                           20

<210> SEQ ID NO 15
<211> LENGTH: 20
<212> TYPE: DNA
<213> ORGANISM: Artificial
<220> FEATURE:
<223> OTHER INFORMATION: PCR primer

<400> SEQUENCE: 15
tcaccaactg ggacgacatg                                           20

<210> SEQ ID NO 16
<211> LENGTH: 19
<212> TYPE: DNA
<213> ORGANISM: Artificial
<220> FEATURE:
<223> OTHER INFORMATION: PCR primer

<400> SEQUENCE: 16
accggagtcc atcacgatg                                            19
```

<210> SEQ ID NO 17
<211> LENGTH: 20
<212> TYPE: DNA
<213> ORGANISM: Artificial
<220> FEATURE:
<223> OTHER INFORMATION: PCR primer

<400> SEQUENCE: 17
gagtttcaac ggcggaggaa                                              20

<210> SEQ ID NO 18
<211> LENGTH: 20
<212> TYPE: DNA
<213> ORGANISM: Artificial
<220> FEATURE:
<223> OTHER INFORMATION: PCR primer

<400> SEQUENCE: 18
agcagaggaa gaagcacacc                                              20

<210> SEQ ID NO 19
<211> LENGTH: 20
<212> TYPE: DNA
<213> ORGANISM: Artificial
<220> FEATURE:
<223> OTHER INFORMATION: PCR primer

<400> SEQUENCE: 19
ggcgtgctgg gtaatcttat                                              20

<210> SEQ ID NO 20
<211> LENGTH: 20
<212> TYPE: DNA
<213> ORGANISM: Artificial
<220> FEATURE:
<223> OTHER INFORMATION: PCR primer

<400> SEQUENCE: 20
caaaggttgt acagctcctg                                              20

<210> SEQ ID NO 21
<211> LENGTH: 20
<212> TYPE: DNA
<213> ORGANISM: Artificial
<220> FEATURE:
<223> OTHER INFORMATION: PCR primer

<400> SEQUENCE: 21
gctacgccct catatttatc                                              20

<210> SEQ ID NO 22
<211> LENGTH: 20
<212> TYPE: DNA
<213> ORGANISM: Artificial
<220> FEATURE:
<223> OTHER INFORMATION: PCR primer

<400> SEQUENCE: 22
gaggttatag aggtcctgcg                                              20

<210> SEQ ID NO 23
<211> LENGTH: 18
<212> TYPE: DNA
<213> ORGANISM: Artificial
<220> FEATURE:

```
<223> OTHER INFORMATION: PCR primer

<400> SEQUENCE: 23
atgaaatcta tgttggtc                                              18

<210> SEQ ID NO 24
<211> LENGTH: 17
<212> TYPE: DNA
<213> ORGANISM: Artificial
<220> FEATURE:
<223> OTHER INFORMATION: PCR primer

<400> SEQUENCE: 24
ccaacgcgcg ggaaggc                                               17

<210> SEQ ID NO 25
<211> LENGTH: 20
<212> TYPE: DNA
<213> ORGANISM: Artificial
<220> FEATURE:
<223> OTHER INFORMATION: PCR primer

<400> SEQUENCE: 25
gcgtcggtca attcaatctt                                            20

<210> SEQ ID NO 26
<211> LENGTH: 20
<212> TYPE: DNA
<213> ORGANISM: Artificial
<220> FEATURE:
<223> OTHER INFORMATION: PCR primer

<400> SEQUENCE: 26
aagctgcaac ctcttcgtca                                            20
```

METHOD OF PREDICTING OBESITY COMPRISING MEASURING NEUROTENSIN

RELATED APPLICATIONS

This application claims the benefit of U.S. Provisional Application Ser. No. 62/299,688, filed Feb. 25, 2016, the entire disclosure of which is incorporated herein by this reference.

STATEMENT OF GOVERNMENT INTEREST

This invention was made with U.S. Government support under contract no. R37 AG10885, R01 DK048498, R01 GM079684, U24 DK097215, R01 ES022191, P01 CA163223, P20 GM103527, R01 HL120507, R01 HL073085, and P20 GM103527 awarded by the National Institutes of Health. The U.S. Government has certain rights in the invention.

TECHNICAL FIELD

The presently disclosed subject matter relates to a method for predicting increased risk of obesity on a non-obese subject. More particularly, the presently disclosed subject matter relates to a method of predicting increased risk of obesity in a non-obese subject by determining a level of neurotensin expression in a biological sample from the subject and comparing the level of neurotensin expression in the sample with a control level.

BACKGROUND

Obesity and its associated comorbid conditions are among the most prevalent and challenging conditions confronting the medical profession in the $21^{st}$ century. Estimates by the World Health Organization indicate that over 1.7 billion people worldwide are overweight (BMI≥25) or obese (BMI≥30) with over 2.5 million deaths annually attributable to obesity. In the U.S., adult obesity rates rose from 14% in 1978 to over 30% in 2000 with over 50% of Americans projected to be obese in 2030. Common comorbidities of over-nutrition and obesity include insulin resistance and the development of hepatic steatosis (i.e., nonalcoholic fatty liver disease, which is noted in about 75% of obese patients). However, the mechanisms responsible for obesity and other metabolic sequelae associated with overconsumption of dietary fats are poorly understood.

The small intestine plays a central role in the control of energy homeostasis through the digestion, absorption and assimilation of ingested nutrients. Food ingestion is associated with the increased secretion of multiple gut peptides, produced in specialized enteroendocrine cells scattered along the length of the small bowel, that act on distant target sites (e.g., liver, muscle and adipose tissue) to promote the efficient uptake and storage of energy, and the regulation of lipid and glucose homeostasis. While GI hormones can regulate energy balance in a number of ways, the role that gut hormones play in obesity and metabolic disorders is poorly understood.

Accordingly, methods for predicting increased risk of obesity in non-obese subjects is desirable.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a method of predicting increased risk of obesity in a non-obese subject, comprising contacting a biological sample from the subject with a probe for neurotensin to determine the amount of neurotensin in the biological sample; comparing the amount of neurotensin to a control level; and determining that the subject has an increased risk of obesity if there is a measurable difference in the amount of neurotensin in the sample as compared to control level, wherein an increased neurotensin level is predictive of an increased risk of becoming obese. In one embodiment, the method further comprises measuring the phosphorylation level of AMPK in the biological sample; and comparing the measured phosphorylation level to a control level, wherein a decreased level of phosphorylation level is predictive for an increased risk of becoming obese. In another embodiment, the biological sample comprises blood, plasma, serum, plasma, and tissue. In a further embodiment, the risk of becoming obese is independent of baseline body mass index.

In some embodiments, the neurotensin is pro-neurotensin, which may be detected by a technique comprising RNA measuring assays and protein measuring assays. One suitable RNA measuring assay comprises real time reverse transcription polymerase chain reaction. The obesity may include, but is not limited to, prevalent obesity, prevalent abdominal obesity, and/or new-onset obesity. Additionally or alternatively, the method further comprises administering to the non-obese subject preventative treatment for obesity. In one embodiment, the preventative treatment includes administration of a neurotensin inhibitor.

In some embodiments, the presently-disclosed subject matter includes a method of detecting reduced intestinal fat absorption in a subject, comprising contacting a biological sample from the subject with a probe for neurotensin to determine the amount of neurotensin in the biological sample; comparing the amount of neurotensin to control level; and determining that the subject has reduced intestinal fat absorption if there is a measurable difference in the amount of neurotensin in the sample as compared to control level, wherein a decreased neurotensin level is indicative of reduced intestinal fat absorption. In one embodiment, the method further comprises measuring the phosphorylation level of AMPK in the biological sample; and comparing the measured phosphorylation level to a control level, wherein an elevated phosphorylation level is indicative of reduced intestinal fat absorption.

In some embodiments, the presently-disclosed subject matter includes a method of preventing and/or treating obesity in a subject in need thereof, comprising administering to the subject an effective amount of an agent that inhibits neurotensin. In one embodiment, the method further comprises administering a pharmaceutically acceptable carrier. In another embodiment, the agent includes, but is not limited to, a neurotensin inhibitor, a neurotensin receptor antagonist, a small molecule, a peptide, and/or siRNA.

Further features and advantages of the presently-disclosed subject matter will become evident to those of ordinary skill in the art after a study of the description, figures, and non-limiting examples in this document.

BRIEF DESCRIPTION OF THE DRAWINGS

FIGS. 1A-H includes images and graphs showing protective effects of neurotensin (NT)-deficiency on obesity and comorbid conditions. A. Image (upper panel) and graph (lower panel) comparing body weight of male $NT^{+/+}$ and $NT^{-/-}$ mice fed a high-fat diet (HFD). B. Image (upper panel) and graph (lower panel) comparing body weight of female $NT^{+/+}$ and $NT^{-/-}$ mice fed a high-fat diet (HFD). Representative images taken at 24 wks. Body weight (BW) was measured weekly for 22 wks; BW slopes were compared: * $p<0.05$ $NT^{+/+}$ vs. $NT^{-/-}$ mice. Male $NT^{+/+}=18$ and $NT^{-/-}=15$ mice; 54.6 g vs. 42.9 g; female $NT^{+/+}=15$ and $NT^{-/-}=12$ mice; 49.2 g vs. 35.9 g at the end time point. C. Plasma glucose (upper panel) and insulin (lower panel) levels quantified in 24 h-fasted male mice maintained on a LFD or HFD for 24 wks (n=8-10); * $p<0.05$ vs. LFD in $NT^{+/+}$ and $NT^{-/-}$ mice, respectively; † $p<0.05$ vs. HFD in $NT^{+/+}$ mice. D. Blood glucose (BG) during insulin tolerance test (ITT) (left panel) and glucose tolerance test (GTT) (right panel) in 6 h-fasted male mice fed a HFD for 24 wks (n=3); * $p<0.05$ vs. $NT^{-/-}$ mice. E. Gross, H&E and oil red O (ORO) imaging of livers of male mice fed a HFD for 24 wks (n=5). F. Hepatic triglyceride (TG) and cholesterol were analyzed by liquid chromatography-mass spectrometry (LC-MS) in 24 h-fasted male mice fed a HFD for 24 wks (n=3). * $p<0.05$ vs. $NT^{+/+}$ mice. G. H&E staining of epididymal fat from male $NT^{+/+}$ and $NT^{-/-}$ mice fed a LFD or HFD for 24 wks. H. Quantitative analysis of adipocyte area (n=6). * $p<0.05$ vs. LFD in $NT^{+/+}$ and $NT^{-/-}$ mice, respectively; † $p<0.05$ vs. LFD in $NT^{+/+}$ mice; $p<0.05$ vs. HFD in $NT^{+/+}$ mice. All data are mean+/−SD.

FIGS. 2A-M includes images and graphs illustrating NT deficiency reduces intestinal lipid absorption. A. (left panel) Fecal triglyceride (TG) was analyzed in male mice fed a high-fat diet (HFD) for 24 wks (n=3); * $p=0.05$ vs $NT^{+/+}$ mice; (right panel) Fecal weight was measured in male $NT^{+/+}$ and $NT^{-/-}$ mice (n=7-9) fed either normal chow (NC) or HFD for 24 wks; there was no significant difference between genotypes. B. Oil red O (ORO) staining of proximal intestines from male mice (6-mo-old) under normal chow fed with or without olive oil by gavage after overnight fasting (n=3). C. Levels of $^{13}C_{18}$-oleic acid (OA) in male mice (5-mo-old) under normal chow fed with $^{13}C_{18}$-OA mixed in olive oil by gavage after an overnight fast was analyzed by nanospray FT-MS (n=3-4). Left panel, * $p<0.05$ vs. $NT^{+/+}$ mice. Right panel, *† $p<0.05$ vs. 0 h in $NT^{+/+}$ and $NT^{-/-}$ mice, respectively; $p<0.05$ vs. 2 h and 3 h in $NT^{+/+}$ mice. D. ORO staining of proximal intestines from male mice (5-mo-old) following gavage with or without olive oil plus NT after an overnight fast (left panel); TG was quantified (right panel) (n=5). * $p<0.05$ vs. Saline in $NT^{+/+}$ and $NT^{-/-}$ mice, respectively; † $p<0.05$ vs. olive oil in $NT^{-/-}$ mice; ‡ $p<0.05$ vs. olive oil in $NT^{+/+}$ mice. E. Western blot analysis of proximal intestinal mucosa from 24 h-fasted male mice (12-mo-old) maintained on a normal chow (left panel). Densitometric quantification of p-AMPK was normalized to total AMPK and is presented as fold change vs. p-AMPK in $NT^{+/+}$ (right panel, n=9). * $p<0.05$ vs. $NT^{+/+}$. F. Protein extracts from mucosal scrapings of samples were analyzed by western blotting (left panel). Densitometric quantification of p-AMPK was normalized by total AMPK and the graph demonstrates the fold change of p-AMPK vs. saline (right panel, n=8). * $p<0.05$ vs. saline; † $p<0.05$ vs. olive oil alone. G. Human small intestinal cells (FHs74Int) (left panel) and RIE-1 cells (right panel) were treated with the indicated concentrations of oleate for 1 h and lysates were analyzed by western blotting. H. FHs 74 Int cells were pre-treated with or without NT at different dose as indicated for 30 min followed by combined treatment with oleate (0.1 mM) for 1 h and western blotting of cell extracts (left panel); densitometric analysis of p-AMPK is from 3 separate experiments and normalized to total AMPK; graph demonstrates the fold change of p-AMPK vs. BSA (right panel). * $p<0.05$ vs. BSA; † $p<0.05$ vs. oleate alone. I. FHs74Int cells transfected with NTR1 (100 nM), NTR3 (20 nM), and control (100 and 20 nM, respectively) for 3 d were treated with oleate (0.1 mM) or BSA in the presence or absence of NT (2 µM) for 1 h and cell extracts were analyzed as in (g). J. FHs 74 Int cells were treated with or without NT (2 µM) for 30 min followed by AICAR (1 mM) for 2 h and oleate (0.1 mM) for 1 h and analyzed by western blot (left panel); p-AMPK levels were determined as in (h) from 3 separate experiments (right panel). * $p<0.05$ vs. BSA; † $p<0.05$ vs. oleate alone; ‡ $p<0.05$ vs. oleate+AICAR. K. FHs74Int cells were treated with NT (2 µM) for 30 min followed by addition of AICAR (1 mM) for another 3 h; cells were then incubated with BSA or BODIPY® FL $C_{16}$ ($C_{16}$) for 15 min and images taken by confocal microscopy. L. FHs74Int cells transfected with LKB1, CaMKK2 and control (all 40 nM) siRNAs for 3 d were treated with oleate (0.1 mM) or BSA in the presence or absence of NT (2 µM) for 1 h and cell extracts were analyzed as in (g). M. FHs74Int cells transfected with Flag-CaMKK2 and control vector for 48 h were treated with or without oleate (0.1 mM) or NT (2 µM) and analyzed by western blotting. p-AMPK levels were determined as in (g) from 3 separate experiments (right panel). * $p<0.05$ vs. BSA in vector- and CaMKK2-transfected cells, respectively; † $p<0.05$ vs. BSA in vector-transfected cells; ‡ $p<0.05$ vs. oleate in vector-transfected cells; # $p<0.05$ vs. BSA in vector-transfected cells; & $p<0.05$ vs. NT alone in vector-transfected cells; § $p<0.05$ vs. oleate+NT in vector-transfected cells. All data are mean+/−SD. Experiments in vitro were at least repeated three times.

FIGS. 3A-G includes images and graphs showing NT suppresses adenosine monophosphate-activated protein kinase (AMPK) activation and promotes lipid accumulation in Drosophila. A. Midguts from 7 d adults expressing Gr36C-Gal4 (control, 100%, n=5)) or Gr36C-NT (93%, n=15) were stained with Nile Red. B. Oenocytes on the basal surface of the lateral epidermis of $3^{rd}$ instar larvae expressing Gr36C-Gal4 (control, 100%, n=15) or Gr36C-NT (93%, n=15) were stained with Oil Red O (ORO) to monitor lipid accumulation. C. Fat bodies attached to the salivary gland from the $3^{rd}$ instar larvae expressing Gr36C-Gal4 (100%, n=8) or Gr36C-NT (100%, n=8) were photographed using DIC microscopy. D. Flies with the indicated genotypes were treated with either normal food (NF) or high-fat diet (HFD), and guts were stained with Nile Red to examine the accumulation of lipids (arrows). Shown here are representative images from each group (n=5). E. NT was expressed by voila-Gal4 and adult flies fed either NF or HFD were subjected for triglyceride (TG) analysis and normalized with protein concentration[38] (n=25 per group). * $p<0.05$ vs. NF in control- and NT-expressing flies, respectively; † $p<0.05$ vs. NF in control-expressing flies; ‡ $p<0.05$ vs. HFD in control-expressing flies. F. Western blotting shown to monitor the levels of AMPK in adult midgut same as (A). G. Myo1A-Gal4 combined with tub-Gal80[ts] (Myo[ts]) does not express Gal4 at 20° C. permissive temperature. Shown in the left panel is the midgut from a 7 d adult bearing Myo[ts]-AMPK raised at 20° C., stained with Nile Red, and used as a control (100%, n=15). Midguts expressing AMPK (middle panel, 100%, n=15) or AMPK RNAi[25931] (right panel, 87%, n=15) from 7 d adults at 29° C. were stained with Nile Red. The levels of AMPK were monitored by western blot.

FIGS. 4A-J shows NT deficiency inhibits high-fat diet (HFD)-induced obesity. A. Epididymal fat pad (arrows) from male mice (5-mo-old) maintained on a normal chow before dissection. B. Epididymal fat pad from male mice (5-mo-old) maintained on a normal chow after dissection. C. Retroperitoneal fat pad from male mice (5-mo-old) maintained on a normal chow (arrows). D. Representative epididymal (arrows) fat pads of male mice fed a HFD for 24 wks. E. Representative retroperitoneal fat pads of male mice fed a HFD for 24 wks. F. Representative pericardial fat pads of male mice fed a HFD for 24 wks. G. Weekly body weight changes of male and female mice placed on a LFD for 25 wks. Male $NT^{+/+}$ n=13, $NT^{-/-}$ n=13 mice; female $NT^{+/+}$ n=12, $NT^{-/-}$ n=14 mice. There is no statistical significance between $NT^{+/+}$ and $NT^{-/-}$ in both male and female mice. H. Fat composition was measured by EchoMRI in male mice fed LFD or HFD for 24 wks (n=5). *$p<0.05$ vs. LFD fat; †$p<0.05$ vs. $NT^{+/+}$ LFD fat; ‡ $p<0.05$ vs. $NT^{+/+}$ HFD fat; #$p<0.05$ vs. $NT^{+/+}$ HFD lean. I. H&E staining of epididymal fat pad from male mice as in FIG. 1g; arrows showing the inflammatory cells. J. F4/80 IHC staining of epididymal fat pad from HFD-fed mice as in FIG. 1g; arrows showing F4/80+ cells. All data are mean+/−SD.

FIGS. 5A-G includes graphs showing NT deficiency does not alter food intake, energy intake, energy expenditure, locomotor activity and resting respiratory exchange ratio (RER). A. Graphs showing cumulative food intake of male (left panel) and female (right panel) mice fed LFD and HFD. Analysis of cumulative food intake for 22 wks did not show a significant difference except in female mice fed HFD (p=0.04). B. Graphs showing weekly food intake of male mice on LFD (left panel) and HFD (right panel). C. Graphs showing weekly food intake of female mice on LFD (left panel) and HFD (right panel). For weekly food intake, there was no significant difference between genotypes in male mice on both diets (B) and female mice fed LFD (C, left panel); food intake on week 9 in female mice fed HFD reached significance between genotypes (C, right panel). For A-C, food intake was measured weekly for $NT^{+/+}$ and $NT^{-/-}$ male (LFD n=3 and HFD n=4) and female (LFD n=3 and HFD n=4) mice. D. Energy expenditure of male mice on LFD and HFD diets for 24 weeks, presented by the average kcal/h in 24 h and in resting period. E. Locomotor activity of male mice on LFD and HFD diets for 24 weeks, which represents counts of beam breaks in a 30 min-period. F. Energy intake of male mice on LFD and HFD diets for 24 weeks, which represents the food intake in kcal for 24 h. G. Resting RER of male mice on LFD and HFD diets for 24 weeks. In D-G, male mice on LFD and HFD diets for 24 wks were placed in individual cages and indirect calorimetric analysis performed (n=10). ANCOVA test, * $p<0.05$ vs. LFD in $NT^{+/+}$ mice; † $p<0.05$ vs. LFD in $NT^{-/-}$ mice. All data are mean+/−SD.

FIGS. 6A-C includes images and graphs illustrating Neurotensin receptor (NTR) expression in small bowel. A. Expression of NTR1 (left panel) and NTR3 (right panel) was analyzed by western blot from mucosa scraped from mouse proximal (pro), middle (mid), distal (dis) small bowel and colon as well as human duodenum (duo) and colon. Proteins from HepG2 (a human hepatocellular carcinoma cell line) and Caco-2 (a human colon cancer cell line) cells stably expressing NTR1, NTR3, or control (NTC) shRNA were used as positive and negative controls. B. IHC was performed on mouse proximal intestines for NTR1 and NTR3 expression. C. Total RNA was isolated from human (FHs74Int) and rat (RIE-1) small intestinal epithelial cells and RT-PCR performed using specific primers targeting human or rat NTR1, 2 and 3.

FIGS. 10A-E shows CG9918 (mouse NTR1 analog) RNAi blocks the NT-mediated decrease of p-AMPK levels in Drosophila S2 cells. A. S2 cells were transfected with ub-Gal4 plus UAST-NT (ub-Gal4-NT) or control (ub-Gal4) vector and treated with the indicated dsRNA to knockdown individual receptors. Cell lysates were subjected to western blot with the indicated antibodies to examine the activation of AMPK (left panel). The efficiency of RNAi knockdown was monitored by real time-PCR (middle panel). * p<0.05 vs. control dsRNA. Medium from cells expressing either ub-Gal4 alone or ub-Gal4-NT was collected to examine the levels of NT by NT EIA (right panel); * p<0.05 vs. ub-Gal4. B. S2 cells were treated with the indicated concentrations of NT peptide for 1 h and AMPK activation was monitored as in (a). NT treatment (0.2, 0.5 µM) decreased p-AMPK to levels similar to those observed in ub-Gal4-NT transfected cells where NT levels reach approximately the same concentration (350 ng/ml, 0.2 µM). C. S2 cells were transfected with ub-Gal4-NT or control vector and treated with the indicated dsRNA and cell lysates were analyzed as in (a). Inactivation of Capability (Capa, CG15520), the Pyrokinin-1 in Drosophila, alters the levels of p-AMPK in neither the presence nor the absence of NT (left panel), indicating that NT prevents AMPK activation independently of Pyrokinin. Capa RNAi efficiency was monitored by real time-PCR (right panel). * p<0.05 vs. control dsRNA. D. Midguts of $3^{rd}$ instar larvae from the indicated genotypes were stained with Bodipy to monitor the accumulation of lipid droplets. Left panel, w1118 control midgut accumulates low level of lipid (100%, n=8). Middle panel, larval midgut constitutively expressing NT by the TK promoter (TK-NT) accumulates high levels of lipid (100%, n=8). Right panel, larval midgut co-expressing TK-NT and Myo1A-CG9918RNAi[27539] accumulated much lower levels of lipid (87%, n=15) compared to TK-NT midgut (middle panel). E. Amino acid sequence alignment of mouse NTR1 (SEQ ID NO: 1) and Drosophila CG9918 (SEQ ID NO: 2), identities and conserved residues (+) are indicated. All data are mean+/−SD. Experiments in vitro were repeated at least three times.

FIGS. 11A-F show graphs illustrating that NT deficiency does not affect body length or small intestine morphology. A. Body length of both $NT^{+/+}$ and $NT^{-/-}$ mice was measured and did not differ significantly between genotypes for either male or female mice (n=12-13/genotype/sex). B. Average weight of the small intestine for male $NT^{+/+}$ and $NT^{-/-}$ mice (n=7/genotype). C. Average length of the small intestine for male $NT^{+/+}$ and $NT^{-/-}$ mice (n=7/genotype). D. H&E staining of proximal intestinal samples from male $NT^{+/+}$ and $NT^{-/-}$ mice (bar=50 µm). E. Villus height measurements from proximal intestinal samples of male $NT^{+/+}$ and $NT^{-/-}$ mice, which show no significant differences between genotypes. F. Crypt number measurements from proximal intestinal samples of male $NT^{+/+}$ and $NT^{-/-}$ mice, which show no significant differences between genotypes. Mice (7 months) for all experiments were maintained on standard chow after weaning and all data are plotted as mean+/−SD.

FIGS. 12A-C show graphs and images illustrating that NT deficiency improves insulin/Akt signaling and reduces adipocyte inflammation. A. $NT^{+/+}$ and $NT^{-/-}$ mice fed LFD or HFD for 22 wks after weaning were fasted overnight. Saline or insulin (5 units) was injected into the IVC. Five min after the injection, liver tissues were collected and protein extracts analyzed by western blot. A representative result is shown from 3 separate experiments. B. Male $NT^{+/+}$ and $NT^{-/-}$ mice (7-mo-old) fed standard chow after weaning were fasted overnight followed by glucose (2 mg/kg) administration by gavage (n=5/genotype). Blood samples were collected both prior to and at the indicated times after glucose administration for measurement of plasma insulin (left panel) and glucose (right panel) levels. No statistically significant differences in either insulin or glucose levels were apparent between genotypes. C. Male $NT^{+/+}$ and $NT^{-/-}$ mice (12-mo-old) fed standard diet after weaning were fasted for 16 h or fasted for 16 h and refeed for 4 h (n=3/genotype). Blood was collected from IVC and plasma used to measure insulin. * p<0.05 vs. fasted $NT^{+/+}$ mice.

FIGS. 13A-D show graphs and images illustrating that NT promotes intestinal cell lipid absorption or accumulation, while NT deficiency reduces intestinal lipid absorption A. Proximal intestines from mice given saline, olive oil, or olive oil+SR 48692 were collected and TG levels quantified as described above (n=8). Graph presents the fold change vs. control mice. * p<0.05 vs. control mice; † p<0.05 vs. mice with olive oil only. B. Male $NT^{+/+}$ and $NT^{-/-}$ mice (n=4) on normal chow were fasted overnight. Mice were injected with either saline or SR 48692 (2.5 mg/kg, i.p). Thirty min after the injection, mice were given olive oil (10 µl/g) by oral gavage and then sacrificed. The proximal small bowel was excised and TG content measured. *p<0.05 vs. saline in $NT^{+/+}$ and $NT^{-/-}$ mice; † p<0.05 vs. olive oil only in $NT^{+/+}$ mice; ‡ p<0.05 vs. olive oil only in $NT^{+/+}$ mice. C. Weekly body weight was measured in male wild type C57BL/6 mice fed HFD and treated with SR 48692 (2.5 mg/kg diluted in diH$_2$O and administered by oral gavage twice a day) or vehicle (vehicle n=12; SR 48692 n=13). BW slopes were compared: * p<0.05 vehicle vs. SR treatment. D. Weekly food intake was measured in male wild type C57BL/6 mice (n=12-13) fed HFD and chronically treated with either SR 48692 or vehicle. Analyses of either cumulative (left panel) or weekly (right panel) food intake did not show a significant difference. All data are mean+/−SD.

FIGS. 14A-C show graphs and images illustrating that FFA activates AMPK signaling and increases NT secretion. A. Plasma NT of male C57BL/6 mice (5-mo-old, n=5) 1 h after olive oil (OO) oral gavage. *p<0.05 vs. NC; n=5. B. NT EIA (upper panels) and western blotting (lower panels) on BON cells treated with or without OA for 1 h. C. NT EIA (upper panels) and western blotting (lower panels) on QGP-1 cells treated with or without OA for 1 h. *p<0.05 vs. control; n=6. All data are mean+/−SD.

FIGS. 15A-B show graphs and images illustrating that FFAR1 and FFAR4 agonists increase AMPK activity. A. NT IF (left panel), NT EIA (middle panel, *p<0.05 vs. control) and western blotting (right panel) of STC-1 cells. B. Real-time PCR. GAPDH was used as the internal control (BON cell expression was arbitrarily set at 1). All data are mean+/−SD.

FIGS. 16A-D show graphs and images illustrating Cross-talk of AMPK and mTORC1 signaling. A. Diagram of cross-talk of AMPK and mTORC1 signaling. B. Western blot analysis of BON cells treated with or without AICAR (left panel) or 1 mM AICAR and CC (10 μM) (right panel) for 3 h. C. NT EIA (upper panel) and western blotting (lower panel) on BON cells expressing control vector and myc-raptor S722A/S792A treated with AICAR (1 mM) for 3 h. D. NT EIA (upper panel) and western blotting (lower panel) on BON cells expressing control vector and NTC and TSC2 siRNA treated with AICAR (1 mM) for 3 h. *p<0.05 vs. control in vector, †p<0.05 vs. AICAR in vector (C); *p<0.05 vs. control in NTC siRNA, †p<0.05 vs. control in NTC siRNA, ‡ p<0.05 vs. AICAR in NTC siRNA (D). n=6. All data are mean+/−SD.

DESCRIPTION OF EXEMPLARY EMBODIMENTS

Figure 2A:
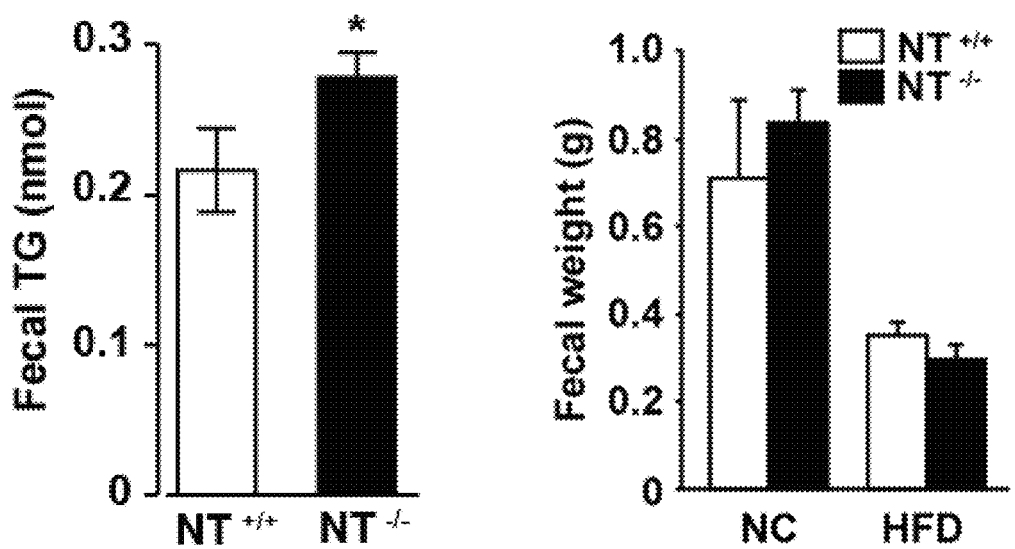

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK®/GENPEPT® accession numbers. The sequences cross-referenced in the GENBANK®/GENPEPT® database are expressly incorporated by reference as are equivalent and related sequences present in GENBANK®/GENPEPT® or other public databases. Also expressly incorporated herein by reference are all annotations present in the GENBANK®/GENPEPT® database associated with the sequences disclosed herein. Unless otherwise indicated or apparent, the references to the GENBANK®/GENPEPT® database are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently disclosed subject matter relates to a method for predicting increased risk of obesity in a non-obese subject. More particularly, the presently disclosed subject matter relates to a method of predicting increased risk of obesity in a non-obese subject by determining a level of neurotensin expression in a biological sample from the subject and comparing the level of neurotensin expression in the sample with a control level.

In some embodiments of the presently disclosed subject matter, a method of predicting increased risk of obesity in a non-obese subject is provided. The method includes the steps of contacting a biological sample from the subject with a probe for neurotensin to determine the amount of neurotensin in the biological sample; comparing the amount of neurotensin to a control level; and determining that the subject has an increased risk of obesity if there is a measurable difference in the amount of neurotensin in the sample as compared to a control level, wherein an increased neurotensin level is predictive for an increased risk of becoming obese.

In some embodiments, the method further includes the steps of measuring the phosphorylation level of AMPK in the biological sample; and comparing the measured phosphorylation level to a control level, wherein a decreased level of phosphorylation is predictive for an increased risk of becoming obese. A non-limiting example of neurotensin is pro-neurotensin. In some embodiments of the presently disclosed subject matter, the risk of becoming obese is independent of baseline body mass index (BMI).

As used herein, the term "obesity" or "obese" refers to a medical condition in which excess body fat has accumulated to the extent that it may have an adverse effect on health, leading to reduced life expectancy and/or increased health problems. Obesity is typically determined by assessing the body mass index (BMI), a measurement which compares weight and height. For example, people are often defined as underweight if BMI is below about 18, normal if BMI is between about 18 and 25, overweight if their BMI is between about 25 and 30, and obese when BMI is greater than about 30. The term "non-obese" refers to underweight, normal, and overweight.

The phrase "predicting increased risk" as used herein refers to methods by which the skilled artisan can predict the course or outcome of the treatment for a condition in a subject. It does not refer to the ability to predict the course or outcome of a condition with 100% accuracy, or even that a given course or outcome is predictably more or less likely to occur based on the presence, absence or levels of test biomarkers. Instead, the skilled artisan will understand that the term refers to an increased probability that a certain course or outcome will occur; that is, that a course or outcome is more likely to occur in a subject exhibiting a given condition, when compared to those individuals not exhibiting the condition (e.g., biomarker level). For example, in individuals not exhibiting the condition, the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a biomarker level (e.g., quantity of expression in a sample) of greater than a control level in some embodiments can signal that a subject is more likely to develop obesity in a non-obese subject than subjects with a level less than or equal to the control level, as determined by a level of statistical significance. Additionally, a change in marker concentration from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments of the presently-disclosed subject matter, a threshold degree of change in the level of a prognostic or diagnostic biomarker can be established, and the degree of change in the level of the indicator in a biological sample can simply be compared to the threshold degree of change in the level. A preferred threshold change in the level for markers of the presently-disclosed subject matter is about 5%, about 10%, about 15%, about 20%, about 25%, about 30%, about 50%, about 75%, about 100%, and about 150%.

In certain embodiments, a diagnostic or prognostic biomarker is correlated to a condition or disease by merely its presence or absence. In other embodiments, a threshold level of a diagnostic or prognostic biomarker can be established, and the level of the indicator in a subject sample can simply be compared to the threshold level.

The "amount" of test biomarker(s) determined refers to a qualitative (e.g., present or not in the measured sample), quantitative (e.g., how much is present), or both measurement of the text biomarker(s) (e.g., neurotensin). The "control level" is an amount (including the qualitative presence or absence) or range of amounts of biomarker(s) found in a comparable biological sample in non-obese subjects who did not become obese. In some embodiments, the control level can refer to reference value or a standard sample that is provided based on information obtained about the amounts of the biomarker(s) found in comparable biological sample(s) from non-obese subjects who did not become obese.

As used herein, the term "subject" refers to an animal, including a mammal, such as a human being.

With regard to the step of providing a biological sample from the subject, the term "biological sample" as used herein refers to any body fluid or tissue potentially comprising the presently-disclosed biomarkers, including neurotensin. In some embodiments, for example, the biological sample can be a blood sample, a serum sample, a plasma sample, or sub-fractions thereof. In some embodiments, the biological sample is an adipose tissue biopsy, such as a tissue biopsy containing adipocytes or cells suspected to be adipocyte.

Turning now to the step of identifying one or more markers in the biological sample, various methods known to those skilled in the art can be used to identify the one or more markers in the provided biological sample. In some embodiments, determining the amount of biomarkers in samples comprises using an RNA measuring assay to measure mRNA encoding biomarker polypeptides in the sample and/or using a protein measuring assay to measure amounts of biomarker polypeptides in the sample.

In certain embodiments, the amounts of biomarkers can be determined by probing for mRNA of the biomarker in the sample using any RNA identification assay known to those skilled in the art. Briefly, RNA can be extracted from the sample, amplified, converted to cDNA, labeled, and allowed to hybridize with probes of a known sequence, such as known RNA hybridization probes (selective for mRNAs encoding biomarker polypeptides) immobilized on a substrate, e.g., array, or microarray, or quantitated by real time PCR (e.g., quantitative real-time PCR). Because the probes to which the nucleic acid molecules of the sample are bound are known, the molecules in the sample can be identified.

With regard to determining amounts of biomarker polypeptides in samples, in some embodiments, mass spectrometry and/or immunoassay devices and methods can be used to measure biomarker polypeptides in samples, although other methods are well known to those skilled in the art as well. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Thus, in certain embodiments of the presently-disclosed subject matter, the marker peptides are analyzed using an immunoassay. The presence or amount of a marker (e.g., neurotensin or pro-neurotensin) can be determined using antibodies or fragments thereof specific for each marker and detecting specific binding. For example, in some embodiments, the antibody specifically binds pro-neurotensin, which is inclusive of antibodies that bind the full-length peptide, fragments thereof, or phosphorylated forms thereof. In some embodiments, the antibody is a monoclonal antibody.

Any suitable immunoassay can be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

In some embodiments, the amount of pro-neurotensin is detected by a technique comprising RNA measuring assays and protein measuring assays. In some embodiments, an RNA measuring assay comprises real time reverse transcription polymerase chain reaction.

In some embodiments, the obesity is prevalent obesity. In some embodiments, the obesity is prevalent abdominal obesity. In some embodiments, the obesity is new-onset obesity.

Further provided in some embodiments of the presently disclosed subject matter, is a method of administering to non-obese subject preventative treatment for obesity. In some embodiments, the preventative treatment includes administration of a neurotensin inhibitor.

In some embodiments, the presently disclosed subject matter further provides a method of detecting reduced intestinal fat absorption in a subject. The method includes the steps of contacting a biological sample from the subject with a probe for neurotensin to determine the amount of neurotensin in the biological sample; comparing the amount of neurotensin to a control level; and determining that the subject has reduced intestinal fat absorption if there is a measurable difference in the amount of neurotensin in the sample as compared to the control level, wherein a decreased neurotensin level is indicative of reduced intestinal fat absorption. In some embodiments, the method further includes the steps of measuring the phosphorylation level of AMPK in the biological sample; and comparing the measured phosphorylation level to a control level, wherein an elevated phosphorylation level is indicative of reduced intestinal fat absorption.

Still further, in some embodiments of the presently disclosed subject matter, a method of preventing and/or treating obesity in a subject in need thereof is provided. The method includes administering to the subject an effective amount of an agent that inhibits neurotensin. In some embodiments, the method further includes administering a pharmaceutical composition including an agent that inhibits neurotensin and a pharmaceutically acceptable carrier. In some embodiments, the agent is a neurotensin inhibitor. In some embodiments, the agent is a neurotensin receptor antagonist. In some embodiments, the agent is a small molecule. In some embodiments, the agent is a peptide. In some embodiments, the agent is neurotensin siRNA.

Non-limiting examples of neurotensin receptor antagonists are those disclosed in Gully et al., 1993 and Gully et al., 1997, including SR 48692 and SR 142948A. Gully et al., 1993, and Gully et al., 1997 are incorporated by reference in their entirety.

As used herein, the terms "treatment" or "treating" relate to any treatment of a condition of interest, including but not limited to prophylactic treatment and therapeutic treatment.

The terms relate to medical management of a subject with the intent to substantially cure, ameliorate, stabilize, or substantially prevent a condition of interest (e.g., disease, pathological condition, or disorder), including but not limited to prophylactic treatment to preclude, avert, obviate, forestall, stop, or hinder something from happening, or reduce the severity of something happening, especially by advance action.

As such, the terms treatment or treating include, but are not limited to: inhibiting the progression of a condition of interest; arresting or preventing the development of a condition of interest; reducing the severity of a condition of interest; ameliorating or relieving symptoms associated with a condition of interest; causing a regression of the condition of interest or one or more of the symptoms associated with the condition of interest; and preventing a condition of interest or the development of a condition of interest.

The terms includes active treatment, that is, treatment directed specifically toward the improvement of a condition of interest, and also includes causal treatment, that is, treatment directed toward removal of the cause of the condition of interest. In addition, the terms includes palliative treatment, that is, treatment designed for the relief of symptoms rather than the curing of the condition of interest; preventative treatment, that is, treatment directed to minimizing or partially or completely inhibiting the development of the associated condition of interest; and supportive treatment, that is, treatment employed to supplement another specific therapy directed toward the improvement of the associated condition of interest.

Neurotensin (NT), a 13-amino acid peptide, or tridecapeptide, predominantly localized in specialized enteroendocrine (EE) cells of the small bowel and released by fat ingestion, facilitates fatty acid (FA) translocation in rat intestine, and stimulates growth of various cancers. NT, which is released from N-cells of the small bowel in response to intraluminal fats, facilitates free fatty acid (FFA) absorption from the intestinal lumen, stimulates pancreaticobiliary secretions, decreases gastric motility, and contributes to lipid metabolism and glucose control, although its precise role in these processes has not been previously delineated. The effects of NT are mediated through three known NT receptors (NTR1, 2 and 3). Increased fasting plasma levels of pro-NT (a stable NT precursor fragment produced in equimolar amounts relative to NT) are associated with increased risk of diabetes, cardiovascular disease and mortality; however, a role for NT as a causative factor in these diseases is unknown. In the past, NT has been considered as a satiety hormone which could potentially curb appetites. Therefore, previous studies have proposed using NT analogues, instead of inhibitor, as a possible treatment for obesity. However, in some embodiments of the presently disclosed subject matter, a preventive and/or treatment method for obesity is provided by administering agents that blocks the effects of neurotensin.

The presently-disclosed subject matter is further illustrated by the following specific but non-limiting examples. The following examples may include compilations of data that are representative of data gathered at various times during the course of development and experimentation related to the presently disclosed subject matter.

EXAMPLES

Example 1

The current study shows that NT-deficient mice demonstrate significantly reduced intestinal fat absorption and are protected from obesity, hepatic steatosis, and insulin resistance associated with high fat consumption. It further demonstrates that NT attenuates the activation of AMP-activated protein kinase (AMPK) and stimulates FA absorption in mice and in cultured intestinal cells, and that this occurs through a mechanism involving NTR1 and NTR3/sortilin in vitro. Consistent with the findings in mice, expression of NT in Drosophila midgut EE cells results in increased lipid accumulation in the midgut, fat body, and oenocytes (specialized hepatocyte-like cells) and decreased AMPK activation. In humans, this study shows that both obese and insulin-resistant subjects have elevated plasma concentrations of pro-NT, and in longitudinal studies among non-obese subjects, high levels of pro-NT denote a doubling of the risk of developing obesity later in life. This study directly link NT with increased fat absorption and obesity and suggest that NT may provide a prognostic marker of future obesity and a potential target for prevention and treatment.

Methods

Reagents.

Antibodies for p-AMPKα (2535), AMPKα (2532), and LKB1 (3050) were from Cell Signaling Technology (Danvers, Mass.). Antibodies for NTR1 (sc-374492 for western blotting and sc-25042 for IHC) and NTR3 (sc-30217 for IHC) were from Santa Cruz Biotechnology (Dallas, Tex.). CaMKK2 (ab168818), NTR3 (ab166490 for western blotting), and F4/80 (ab100790) antibodies were from Abcam (Cambridge, Mass.). FLAG (F1804) and β-actin (A5316) antibodies were from Sigma-Aldrich (St. Louis, Mo.). ON-TARGETplus SMARTpool (LKB1, CaMKK2, NTR1, NTR3) and ON-TARGETplus Non-targeting Control Pool siRNA were purchased from GE Dharmacon (Lafayette, Colo.). AICAR was from Cayman (Ann Arbor, Mich.). Oleate sodium, NT, glucose and human insulin were from Sigma. Deuterated oleic acid (CLM-460-PK) was obtained from Cambridge Isotope Laboratories (Tewksbury, Mass.). SR 48692 was from Tocris (Minneapolis, Minn.). siRNA (RNAiMAX) and plasmid (Lipofectamine® LTX Reagent with PLUS™ Reagent) transfection reagents, and Trizol were from Life Technologies (Grand Island, N.Y.). pSG5-FLAG-CaMKK2 rat FL was a gift from Anthony Means (Addgene plasmid #32449) (Cambridge, Mass.). Primers for RT-PCR were from Integrated DNA Technologies (Coralville, Iowa).

Mice.

All procedures were approved by the Institutional Animal Care and Use Committee of the University of Kentucky. NT homozygous ($NT^{-/-}$) mice and their wild type littermates ($NT^{+/+}$) were bred from NT heterozygous ($NT^{+/-}$) mice and randomly grouped for all experiments. Mice were maintained on 12-h light-dark cycles and provided with food and water ad libitum. For diet-induced obesity studies, male and female $NT^{+/+}$ and $NT^{-/-}$ mice were placed on a 60% HFD or 10% LFD (catalogue no. D12492 and D12450B, respectively; Research Diets, New Brunswick, N.J.) at weaning for 22-25 wks. Body weight and food intake were measured weekly. Food intake was measured for each cage (3-5 mice per cage) and divided by mouse number to obtain total grams consumed per mouse per week. All mice used were 4-6 months old unless otherwise indicated. For chronic SR 48692 treatment on HFD-fed mice, C57BL/6 mice (8 weeks old) were obtained from Taconic. After one week acclimation, mice were placed in individual cages, started on HFD, and after one week were divided into 2 groups one of which received SR 48692 (dissolved in sterile $diH_2O$ by brief sonication, 2.5 mg/kg body weight[31-33] and the other vehicle twice/day (8 am and 8 pm) by gavage. Mice were weighed and food intake was measured weekly.

Human Intestinal Samples.

Surgical samples of duodenum and colon were obtained from de-identified donors through the Markey Cancer Center Biospecimen and Tissue Procurement Shared Resource Facility. All samples were obtained after informed consent according to a protocol approved by the Institutional Review Board of the University of Kentucky Medical Center (UKMC). Freshly-resected duodenum and colon specimens were placed in cold (4° C.) Dulbecco's Modified Eagle's Medium (DMEM) (Sigma-Aldrich) supplemented with 10% fetal bovine serum (FBS) (Sigma-Aldrich), 2% penicillin/streptomycin (20,000 U/mL penicillin, 20 mg/mL streptomycin) (Sigma-Aldrich), and 1.0 μg/mL Fungizone (Life Technologies). Tissues were processed within one hour after resection; the mucosal layer was sharply dissected from the underlying seromuscular layer and collected in multiple 3 to 5 mm sections for western blotting.

Cell Culture.

FHs74Int, purchased from ATCC (Manassas, Va.), is a human small intestinal epithelial cell line maintained in Hybri-Care Medium ATCC 46-X supplemented with 30 ng/ml epidermal growth factor (Sigma-Aldrich) and 10% FBS. RIE-1 is a rat intestinal epithelial cell line maintained in DMEM containing 2 mM L-glutamine, 4500 mg/L glucose and 10% FBS. The human colon cancer cell line, Caco-2 (ATCC), is maintained in Minimum Essential Medium (MEM) (Sigma-Aldrich) supplemented with 15% FBS. The human liver cancer cell line, HepG2 (ATCC), is maintained in MEM with 10% FBS. FHs 74 Int cells were tested for authentication via STR profiling in April 2015 by Genetica DNA Laboratories (LabCorp Specialty Testing Group; Burlington, N.C.) using the commercially available PowerPlex® 16HS amplification kit (Promega Corporation) and GeneMapper ID v3.2.1 software (Applied Biosystems). Authentication was confirmed by a 100% match in comparison to the reference STR profile from ATCC (FHs 74 Int; ATCC® CCL-241™). The cell lines are not listed in the ICLAC database. In addition, both cell lines were tested for *mycoplasma* contamination via PCR (e-Myco Plus kit; iNtRON Biotechnology) and were found to be negative.

Western Blotting.

Tissues and cells were lysed with lysis buffer (Cell Signaling Technology), and equal amounts of protein were resolved on 4-12% NuPAGE BisTris gels (Life Technologies) and electrophoretically transferred to polyvinylidene difluoride (PVDF) membranes; the membranes were incubated with primary antibodies overnight at 4° C. followed by secondary antibodies conjugated with horseradish peroxidase. Membranes were developed using chemiluminescence (ECL) Western Blotting System from GE Healthcare Life Science (Piscataway, N.J.) and Thermo Scientific (Waltham, Mass.).

Histology and Immunohistochemistry (IHC).

Epididymal adipose, liver and intestinal tissues were fixed in 10% neutral-buffered formalin, embedded in paraffin, and sectioned (5 μm). H&E staining was performed using standard techniques. Adipocyte size was measured as described previously. Briefly, sections of epididymal adipose tissue from each mouse were photographed under ×100 magnification. In a square measuring 700×700 μm (x- and y-axis, respectively), adipocyte size and number were measured using NIS Elements BR.3.10 software. A criterion for inclusion of measurements was a circularity of adipocytes superior to 0.33 [shape of cells; from 0 (thin shape) to 1 (perfect circle)]. For oil red O (ORO) staining, liver and small bowel tissues were fixed in 10% neutral-buffered formalin, equilibrated in 30% sucrose and embedded in OCT compound and snap-frozen in liquid $N_2$. Frozen sections were stained with ORO (Sigma-Aldrich) for lipid deposition using standard methods. IHC was performed and visualized by Dako EnVision Systems (Burlington, Ontario, Canada) following the product instruction.

Reverse transcription-polymerase chain reaction (RT-PCR). Total RNA was isolated from cells using RNeasy Kit (Qiagen, Valencia, Calif.) according to the manufacturer's instructions. RT-PCR analysis of NTR1, 2 and 3 was performed using cDNA synthesized from 1 μg of total RNA. β-actin was used as the internal control. The primers included: human NTR1:

```
                                     (SEQ ID NO: 3)
5'-TCATCGCCTTTGTGGTCTGCT-3'
and
                                     (SEQ ID NO: 4)
5'-TGGTTGCTGGACACGCTGTCG-3';

human NTR2:
                                     (SEQ ID NO: 5)
5'-GTCTCCTCAGCTTCATCGTAT-3'
and
                                     (SEQ ID NO: 6)
5'-TCCCCAAAGCCTGAAGCTGTA-3';

human NTR3 (SORT1):
                                     (SEQ ID NO: 7)
5'-AGAATGGTCGAGACTATGTTG-3'
and
                                     (SEQ ID NO: 8)
5'-AAGAGCTATTCCAAGAGGTCC-3';

rat ntr1:
                                     (SEQ ID NO: 9)
5'-GAGAAGCCCCCAAAATTCTC-3'
and
                                     (SEQ ID NO: 10)
5'-CAAGGACCCAGTGCAGGTAT-3';

rat ntr2:
                                     (SEQ ID NO: 11)
5'-ACTCGCTCATCTTCGCATTT-3'
and
                                     (SEQ ID NO: 12)
5'-TGGGACCACACGAAGTTGTA-3';

rat ntr3 (Sort1):
                                     (SEQ ID NO: 13)
5'-TTTCAAGCTGTGCTTTGTGG-3'
and
                                     (SEQ ID NO: 14)
5'-AGTTCTCTGAACGGGAGCAA-3'.

β-actin:
                                     (SEQ ID NO: 15)
5'-TCACCAACTGGGACGACATG-3'
and
                                     (SEQ ID NO: 16)
5'-ACCGGAGTCCATCACGATG-3'.
```

The PCR products were analyzed on a 2% agarose gel.

NT Enzymeimmunoassay (EIA).

Fifty μl of media were used to measure NT levels using NT EIA Kit from Phoenix Pharmaceuticals (Burlingame, Calif.) as described previously[30-33].

Glucose and Insulin Tolerance Tests.

Glucose (GTT) and insulin (ITT) tolerance tests were performed on 6 h-fasted mice fed HFD. Glucose values were measured using One Touch Ultra from LifeScan (Wayne, Pa.) by tail snip. Glucose (1.5 g/kg body weight) and human insulin (0.75 U/kg body weight) were injected intraperitoneally (i.p.) after baseline glucose levels established in each mouse. Glucose was measured at 15, 30, 60 and 120 min after injection.

Metabolic Studies.

Whole body composition parameters were measured by EchoMRI-5000 Whole Body Composition (Echo Medical System, Houston, Tex.) using Magnetic Resonance Relaxometry to precisely measure total body fat, lean mass, body fluids and total body water in conscious mice. A TSE LabMaster indirect calorimetry system (TSE-Systems Inc., Chesterfield, Mo.) was used to simultaneously quantify energy expenditure, energy intake, locomotor activity, and respiratory exchange ratio (RER). Mice were acclimated to the chambers for 7 d, to permit recovery from the weight loss initially experienced by obese mice. Recordings were performed for 5 d, yielding three full 24 h periods of data. Feeding and activity data were collected continuously; $O_2$ and $CO_2$ levels for energy expenditure and RER calculations were collected at 30 min intervals. Resting energy expenditure values were calculated from data collected between 9 AM and 6 PM, filtered to remove points at which activity was greater than 150 counts for that interval.

For hepatic triglyceride and cholesterol measurements, liver tissues were collected and triglyceride and cholesterol extracted as described previously and analyzed by LC-MS coupled with electrospray ionization tandem using stable isotope dilution performed on AB Sciex 4000 Q-Trap instruments. Plasma glucose was analyzed using a Glucose Colorimetric Assay Kit (BioVision, Inc., Milpitas, Calif.) and insulin using a Mouse Insulin ELISA kit (Mercodia Inc, Winston Salem, N.C.). Plasma insulin and glucose levels were measured in mice (fed standard chow after weaning) that had been fasted overnight and subsequently given glucose (2 g/kg body weight) by gavage (i.e., oral glucose tolerance test). Blood was collected from tail snips before (0 min) or 15, 30, 60 and 120 min after gavage. Insulin and glucose levels were measured as described above. Plasma insulin levels were also determined in mice that were either fasted for 16 h or fasted for 16 h with refeeding for 4 h; blood was collected from the IVC. For fecal triglyceride assay, mice were housed in individual cages for 4 d; day 4 fecal samples were dried and ground. Lipid was extracted from 50 mg of fecal samples and triglyceride measured by LC-MS and normalized to fecal weight.

Body Length Measurements.

Anal-nasal length was measured following isoflurane anesthesia of $NT^{+/+}$ and $NT^{-/-}$ mice.

Fecal Weight Measurements.

$NT^{+/+}$ and $NT^{-/-}$ mice fed HFD for 24 wks were separated into individual cages and fecal pellets were collected and weighed daily for 4 d. Fecal weights from day 4 were averaged for wild type and NT deficient mice.

Small intestinal characterization. The entire small intestine (SI), from the gastric pylorus to the ileocecal valve was dissected from anesthetized male $NT^{-/-}$ and $NT^{+/+}$ mice. The SI length was measured and then opened longitudinally, washed in cold saline to clear the luminal contents, dried briefly on a paper towel and weighed. The SI was divided 5 cm distal from the pyloric junction and the jejunoileum was divided into equal proximal and distal fragments. Proximal fragments were fixed in 10% neutral-buffered formalin for 24 h, and "Swiss rolls"[41] were sectioned (5 µm) for H&E and IHC staining. H&E stained sections were imaged on an Aperio ScanScope XT™ slide scanner at 20×. Crypt counts and villus height were determined using Aperio ImageScope v11.2.0.780 software. Crypts in a 1 mm field were quantified; 10 fields were analyzed per section. Villus height was measured from 10 well-oriented villi on each slide.

Lipid Absorption Studies.

For olive oil administration and ORO analysis, mice were fasted overnight and fed the olive oil (17 µl/g body weight) by gavage. The mice were sacrificed before (control), 30 min and 60 min after the gavage. The intestine was resected from the ligament of Treitz to the ileocecal junction, divided into proximal, middle, and distal segments of equal length and washed with cold saline. The proximal intestine was processed for frozen sections and ORO staining by standard protocol.

For $^{13}C_{18}$-OA experiments, mice were fasted overnight and fed $^{13}C_{18}$-OA (480 µM/g body weight) mixed in olive oil (10 µl/g body weight) by gavage. Mice were sacrificed at 0 and 30 min after gavage. Proximal intestines were collected. To detect plasma level of $^{13}C_{18}$-OA, mice were given $^{13}C_{18}$-OA as above and blood was collected from tail snip before (0 h), 1, 2 and 3 h after gavage. Lipid was extracted from proximal intestines and plasma and analyzed for $^{13}C_{18}$-OA enrichment by direct infusion nanospray FT-MS (Orbitrap Fusion™ Tribrid™ Mass Spectrometer, Thermo Scientific, Waltham, Mass.) modified from a previous method. Briefly, aliquots of the lipid extracts were first diluted twenty-fold in isopropanol:chloroform:methanol 4:2:1 before introduction into TriVersa NanoMate® (Advion, Inc., Ithaca, N.Y.) and analyzed on the Orbitrap Fusion in negative ion mode to estimate the appropriate amount of $d_{34}$-OA to spike. Lipid extracts spiked with known concentration of $d_{34}$-OA in the same solvent system were analyzed again with the same FT-MS method. The nanospray conditions on the Nanomate were as follows: 15 µl of sample injection, 16 min of delivery time, 0.4 psi of gas pressure, and 1.5 kV of negative applied voltage. The Orbitrap Fusion MS analysis conditions were as follows: mass resolution of 450,000 with lock mass using internal calibrant, scan range of m/z 150-1600, % S-Lens RF Level of 60, 1.0e5 for AGC Target, 100 msec maximum injection time, and 10 averaged microscans. The ion transfer tube temperature was 275° C., and the experimental mass accuracy was ±~1 ppm. The unlabeled, $^{13}C$ labeled, and $d_{34}$-OA were assigned based on their respective accurate mass of 281.24860, 299.30899, and 314.45574; unlabeled and $^{13}C$ labeled OA were then quantified against the internal $d_{34}$-OA standard using their respective peak intensity.

For NT "rescue" experiments, mice were fasted overnight and fed with or without the olive oil (17 µl/g body weight) by gavage followed by i.p. injection of saline or NT (3600 nmol/kg body weight) immediately after gavage. The mice were sacrificed 60 min after the gavage. Partial proximal intestine was processed for ORO staining as described above and partial for triglyceride quantification using a Triglyceride Determination Kit (Sigma-Aldrich)[38].

For in vitro FA absorption or lipid accumulation studies, FHs74Int and RIE-1 cells were incubated with either bovine serum albumin (BSA) (Sigma-Aldrich) or BSA-conjugated BODIPY® FL $C_{16}$ (4,4-Difluoro-5,7-Dimethyl-4-Bora-3a, 4a-Diaza-s-Indacene-3-Hexadecanoic Acid) (Life Technologies) for 15 min. BSA-conjugated oleate sodium was also used to treat cells for 1 h; cells were then stained with BODIPY® 493/503 (4,4-Difluoro-1,3,5,7,8-Pentamethyl-4-Bora-3a,4a-Diaza-s-Indacene) (Life Technologies). Images were observed under an FV1000 Olympus confocal microscope with a ×60, 1.35-numerical aperture oil objective (Olympus, Tokyo, Japan). Images were analyzed with Olympus FV10-ASW2.1 software. To quantify green intensity, 3 images were taken at consistent conditions and 10 cells from each image were analyzed using the area tool. For the lipid accumulation study, RIE-1 cells were pre-treated with or without NT at different concentrations for 30 min followed by combination of NT with BSA or BSA-conjugated oleate (0.1 mM) overnight. Cells were collected, lysed and triglyceride content was measured by Triglyceride Determination Kit (Sigma-Aldrich). All experiments were carried in serum-free medium and fatty acid-free BSA was used at 0.1%.

For acute SR 48692 treatment, male wild type C57BL/6 mice (16 weeks old) obtained from Taconic (Hudson, N.Y.) were acclimated for one week, randomly divided into control, olive oil, and olive oil+SR 48692 groups (n=8) and fasted overnight. SR 48692 was dissolved in DMSO (50 mg/ml) and diluted 1:100 in saline just prior to use. Mice were injected i.p. with SR 48692 (2.5 mg/kg)[31,33] or vehicle 30 min prior to oral gavage of olive oil (10 µl/g), sacrificed after an additional 30 min, and the distal half of the proximal intestine (see above) was used to determine TG content and for preparation of lysates for western blotting. This experiment was repeated in male $NT^{+/+}$ and $NT^{-/-}$ mice (7-mo-old), and proximal intestinal TG was measured as described above.

*Drosophila* Studies.

Full-length human NT cDNA was inserted into an attB-UAST backbone and the resultant transgene generated using an attP2 locus and PhiC31 integration system. UAS-AMPK and UAS-AMPKRNAi (v106200) lines have been described. UAS-AMPKRNAi line was also obtained from Bloomington Stock Center (TRiP #25931). These RNAi (TRiP #25931 and v106200) gave rise to similar phenotypes, thus AMPKRNAi[25931] was used for most of the experiments. Gr36C-Gal4, Myo1A$^{ts}$-Gal4, voila-Gal4, and S106-Gal4 have been described (FlyBase). Myo1A-Gal4 is specifically expressed in enterocytes. In order to constitutively express NT in gut EE cells, a gut EE cell-specific TK promoter (2.0 kb)[28,29] was cloned into attB-UAST lacking Gal4 binding sites followed by insertion of full-length NT cDNA and the resulting plasmid (TK-NT) was used to generate a transgenic line by insertion at the VK5 attP locus. To express NT in EE cells and knock down CG9918 by RNAi in EC cells, the following genotype was used: yw; Myo1A-Gal4/CG9918RNAi[27539]; TK-NT/+. The tub-Gal80$^{ts}$ was used in combination with the Myo1A-Gal4 (resulting in the genotype of Myo$^{ts}$) to temporarily control Myo1A-Gal4 target gene expression, after shifting larvae to 29° C. nonpermissive temperature 96 h after egg laying (AEL) or adult emerging. The present inventors combined the AMPK or AMPKRNAi allele with the RU486-inducible GeneSwitch Gal4 line: S106-Gal4, which is fat body-specific. Then, the present inventors grew larvae with either S106-AMPK or S106-AMPKRNAi to vehicle or RU486 (200 µM, Mifepristone, Sigma-Aldrich) containing food and examined the accumulation of lipid droplets in fat body or oenocytes from 3$^{rd}$ instar larvae. Fresh food was supplied every other day. For midgut immunostaining, midguts from 3$^{rd}$ instar larvae or adults with specific genotypes were dissected in PBS then fixed with 4% formaldehyde in PBS for 20 min. After permeabilization with PBT (PBS supplemented with 0.1% Triton X100), midguts were incubated with the indicated primary antibodies for 3 h and the corresponding secondary antibodies for 1 h sequentially, and washed with PBT for 3 times, 20 min per wash, following incubation. Antibodies used in this study: mouse anti-Pros (DSHB, MR1A); rabbit anti-NT (Abcam, ab43833). Midgut staining with Nile Red (Sigma-Aldrich) and larvae staining with Oil Red O (Sigma-Aldrich) were carried out after fixation.

For western blot analysis, 15 entire gastrointestinal tracts from each genotype were lysed in SDS sample buffer [100 mM NaCl, 50 mM Tris.HCl [pH8.0], 1.5 mM EDTA, 10% glycerol, 1% NP-40, and protease inhibitor tablet (Roche, Indianapolis, Ind.)], and resolved by SDS-PAGE and transferred to PVDF membranes (Millipore). Membranes were blocked and probed with primary antibodies to phospho-AMPKα (Cell Signaling, #2535), total AMPKα (Abcam, ab80039,), and β-tubulin (DSHB, E7, Iowa City, Iowa). After wash and incubation with secondary antibody (Jackson ImmunoResearch, West Grove, Pa.), signals were detected using ECL.

The method of HFD feeding for adult flies has been described. Briefly, flies (5 d after emerging) were collected and placed in bottles of normal food (cornmeal-yeast) and aged for an additional 5 d. This population was then split into two study groups, one on normal food and one on the HFD containing 20% (weight-to-volume ratio) coconut oil with the normal food. Flies were treated on HFD for 5 d. Treated adult flies were dissected and stained with Nile Red to examine lipid accumulation in the midgut. The other group of flies expressing NT by the EE cell-specific voila-Gal4 was subjected to triglyceride measurement (Sigma-Aldrich) after being given either HFD or normal food. voila-Gal4-w1118 flies were used as control for this triglyceride experiment. Both male and female flies showed similar results in triglyceride concentration, which was increased by HFD.

*Drosophila* S2 cells were cultured as previously described. dsRNA was synthesized against GFP (nucleotides 6-606), CG9918 (nucleotides 11~570), CG8784 (nucleotides −72~478), CG8795 (nucleotides −203~343), and Capa (nucleotides 1-455) by the method described. Total RNA was extracted using Trizol reagent (Invitrogen). cDNA was synthesized using SuperScript III First Strand Synthesis kit (Invitrogen) from 1.0 μg total RNA according to the manufacturer's instructions. Quantitative RT-PCR reactions were carried out using SYBR Green PCR master mix reagents (Thermo) on the ABI StepOnePlus Real-Time PCR System (Applied Biosystems). Thermal cycling was conducted at 95° C. for 30 sec, followed by 40 cycles of amplification at 95° C. for 5 sec, 55° C. for 30 sec and 72° C. for 15 sec. The relative quantification of gene expression for each sample was analyzed by the ΔCt method. The following primers were used to amplify:

```
CG9918:
5'-GAGTTTCAACGGCGGAGGAA-3' (SEQ ID NO: 17)
and

5'-AGCAGAGGAAGAAGCACACC-3', (SEQ ID NO: 18)

CG8784:
5'-GGCGTGCTGGGTAATCTTAT-3' (SEQ ID NO: 19)
and

5'-CAAAGGTTGTACAGCTCCTG-3', (SEQ ID NO: 20)
```

-continued
```
CG8795:
5'-GCTACGCCCTCATATTTATC-3' (SEQ ID NO: 21)
and

5'-GAGGTTATAGAGGTCCTGCG-3', (SEQ ID NO: 22)

Capa:
5'-ATGAAATCTATGTTGGTC-3' (SEQ ID NO: 23)
and

5'-CCAACGCGCGGGAAGGC-3', (SEQ ID NO: 24)

Actin:
5'-GCGTCGGTCAATTCAATCTT-3' (SEQ ID NO: 25)
and

5'-AAGCTGCAACCTCTTCGTCA-3' (SEQ ID NO: 26).
```

NT Enzyme Immunoassay (EIA).

Fifty μl of media from S2 cells transfected with ub-Gal4 and UAST-NT were used to measure NT levels using NT EIA Kit from Phoenix Pharmaceuticals (Burlingame, Calif.) as described previously.

LC-MS/MS Analysis of NT.

NT was analyzed by liquid chromatography tandem mass spectrometry (LC-MS/MS) using an LTQ-Orbitrap mass spectrometer (Thermo Fisher Scientific, Waltham, Mass.) coupled with an Eksigent Nanoflex cHiPLC™ system (Eksigent, Dublin, Calif.) through a nano-electrospray ionization source. NT in the NT EIA kit (Phoenix Pharmaceutical) was used as standard. S2 cells were transfected with ub-Gal4 and UAST-NT or the UAST vector control, and conditioned medium was harvested after 48 h for analysis. GI tracts (350/genotype) were dissected from wild-type (w1118) or Gr36C-NT $3^{rd}$ instar larvae, methanol extracted, extracts were dried, and dissolved in 20 μl 0.1% (v/v) formic acid in water for analysis. Samples were separated by reversed phase cHiPLC [ChromXP C18 column, 75 μm I.D.×15 cm length, Eksigent cat#804-00001; mobile phase A and B were 0.1% (v/v) formic acid in either water or acetonitrile, respectively; flow rate, 300 nl/min]. LC-MS/MS data were acquired in an automated data dependent acquisition mode consisting of an Orbitrap MS scan (300-1800 m/z, 60,000 resolutions) followed by MS/MS for fragmentation of the 7 most abundant ions with the collision induced dissociation method. MS/MS fragments corresponding to $NT^{1-13}$ were identified by comparison with the NT standard, and quantified using the intensity of the $NT^{3+}$ peak and NT standards (0.05, 0.1, 0.2, 0.5 fmole).

Human Population Studies.

The Malmö Diet and Cancer (MDC) study is a population-based, prospective epidemiologic cohort of 28,449 men (born 1923-1945) and women (born 1923-1950) from the city of Malmö in southern Sweden who underwent baseline examinations between 1991 and 1996. From this cohort, 6,103 persons were randomly selected to participate in the MDC Cardiovascular Cohort (MDC-CC), which was designed to investigate the epidemiology of carotid artery disease, between 1991 and 1994. Fasted plasma samples at the baseline examination were available for analysis of pro-neurotensin (pro-NT) and successfully measured in a total of 4,632 participants in the MDC-CC. Of those, complete data were available for BMI in 4,626, for waist circumference on 4,625, and for estimated degree of insulin resistance using the homeostasis model assessment of insulin resistance (HOMA-IR) (fasting blood glucose concentration×fasting plasma insulin concentration/22.5) in 4,468 participants. BMI was defined as body weight in kilograms divided by the square of height in meters and obesity as a BMI≥30 kg/m². Abdominal obesity was defined as a waist circumference of ≥94 cm in males and ≥80 cm in females, according to the International Diabetes Federation definition. Insulin resistance was regarded present in subjects belonging to the top 25% of HOMA-IR values in the MDC-CC. 'New-Onset Obesity' is defined as obesity development among non-obese MDC-CC participants who were re-examined and diagnosed with obesity after an average follow-up time of 16.5±1.5 years. Pro-NT was measured in stored fasting plasma specimens that were frozen to −80° C. immediately at the MDC-CC baseline exam using a recent chemiluminometric sandwich immunoassay to detect a pro-NT precursor fragment (pro-NT 1-117) as described previously. Analyses of blood glucose and plasma insulin were carried out at the time of baseline examination at the Department of Clinical Chemistry, Malmö University Hospital, which is attached to a national standardization and quality control system. Of the 4,626 subjects with baseline data on BMI and pro-NT, 2,900 subjects were re-examined with a new measurement of BMI after a mean follow-up of 16.5±1.5 years. In analyses of incident obesity, the present inventors excluded 306 subjects who were obese already at the baseline examination, leaving a total of 2,594 non-obese subjects for analysis of pro-NT in relation to incident obesity. All participants gave written informed consent, and the study was approved by the Ethical Committee at Lund University, Lund, Sweden.

Statistical Analysis.

Descriptive statistics including means and standard deviations were calculated and represented using bar graphs. Linear mixed models were implemented to compare body weight and food intake levels over time as well comparisons at each time point for other endpoints from in vivo experiments involving repeat measurements. Specifically, body weight growth curves were compared using linear mixed models with fixed effects for linear and quadratic terms for time and their interaction with genotype and random effects for the intercept and time factors. Contrast statements for the interaction terms in the model were used to assess differences in growth curves between genotypes. Likewise, linear mixed models were employed for body weight growth curve comparisons between vehicle versus SR 48692 with the same fixed and random effects terms as above along with baseline weight as a covariate. Total food consumption for 22 weeks was calculated and compared between genotypes and between vehicle versus SR 48692 treatment using two-sample t-tests. Furthermore, weekly food intake levels were analyzed using linear mixed models. However, since there is no clear trend in weekly food intake over time, an overall comparison of trend was not employed. Instead, a linear mixed model with fixed effects for genotype, time and their interaction and a random effect for the intercept term was employed in order to perform individual comparisons at each time point. A p-value adjustment due to multiple testing at each time point was performed using the Holm's step-down procedure. We used the Akaike Information Criterion (AIC) to evaluate the goodness-of-fit of the above linear mixed models. One-way or two-way analysis of variance models with test for interaction between two factors was employed for multiple group comparisons of diet (LFD, HFD), mouse genotype, feeding and fasting groups, different time points of measurement, and varying doses of NT treatment, SR 48692 and AICAR treatments with contrasts generated to perform pairwise comparisons. Analysis of covariance was employed to compare genotype and diet with adjustment for the confounding effect of mouse body weight for fat composition and energy metabolism endpoints (energy expenditure, locomotor activity, energy intake, respiratory ratio). Model-building was performed to assess equality of slopes using two-way interactions between each of genotype and diet with the covariate as well as genotype and diet interactions. Two-sample t-test or the nonparametric analog was employed for cell culture and in vivo studies involving two independent groups.

For the animal studies, sufficient sample sizes were utilized to provide at least 80% power to detect large effect sizes (1.0 to 3.0 mean differences in SD units) based on two-group comparisons, two-sided tests with 5% significance level. Some experiments including body weight and food intake were measured repeatedly thus affording larger statistical power. No replicate samples from in vitro studies were excluded in the analysis. All data from animal samples with measurement of study endpoints were included in the analysis. Experiments with slight differences in animal numbers per group were due to the number of animals that were successfully bred and not due to exclusion of certain animals and their data points. Mice within a cage were randomized to all groups in an experiment to ensure balance in treatment group assignments across all cages. The animals were randomly selected for group assignment without preference to size or other confounding factors. A different individual performed measurements on study endpoints to ensure blinding from group assignment. Furthermore, only animal IDs without information on group assignment were available to staff performing the endpoint evaluation. Parametric tests were utilized after evaluating distribution of data (e.g. percentiles, mean and median levels), test for normality (e.g. Kolmogorov-Smirnov test, if sufficient sample sizes) and test for homogeneity of variance assumptions across groups. Otherwise, nonparametric tests were utilized. Appropriateness of other statistical models including linear mixed models to evaluate trends over time and goodness of fit of the models using the Akaike Information Criterion (AIC) and analysis of covariance (ANCOVA) assuming equal slopes between groups were also evaluated.

All subjects at the MDC-CC baseline examination were divided into ascending quartiles according to their value of fasting pro-NT. Body-mass-index (BMI), waist circumference and homeostasis model assessment of insulin resistance (HOMA-IR) were analyzed as dichotomous outcome variables as defined above. In cross-sectional analyses, the present inventors related baseline quartile of pro-NT to the dichotomous outcome of obesity, abdominal obesity, and insulin resistance using age and sex adjusted logistic regression models. In the analyses of incident obesity, the present inventors related baseline quartile of pro-NT to the dichotomous outcome of incident obesity using logistic regression adjusted for baseline age, sex, and BMI. Data are presented as odds ratios (95% confidence intervals), and subjects belonging to the lowest quartile of pro-NT were defined as the referent group (odds ratio=1). 'P for trend' denotes the P-value for linear trend over quartiles 1-4.

Results:

To examine the potential role of NT in fat deposition and obesity, the present inventors initially compared NT-deficient mice to their wild type littermates fed a standard diet (18% kcal from fat) for 6 months. Average body weights, body length, small bowel weight and length, villus height, and crypt number did not differ significantly between genotypes (FIG. 11A-F). However, at necropsy, the epididymal and retroperitoneal fat pads of $NT^{-/-}$ mice were consistently smaller in size as compared to wild type (FIG. 4A-C), which prompted further investigation. Indeed, when challenged with a high-fat diet (HFD; 60% kcal from fat), the size of epididymal, retroperitoneal, and pericardiac fat deposits were markedly smaller in $NT^{-/-}$ mice compared to wild type (FIG. 4D-F). Consistent with these differences in fat deposition, as compared to wild type, both male and female $NT^{-/-}$ mice fed HFD gained less body weight with significant differences first noted at 9 weeks in males (FIG. 1A) and 16 weeks in females (FIG. 1B). In contrast, no differences in body weight were noted between female $NT^{+/+}$ and $NT^{-/-}$ mice fed a low-fat diet (LFD; 10% kcal from fat) (FIG. 4G), similar to what was observed in mice fed standard chow. EchoMRI assessment of total fat (corrected by body weight) further confirmed that body fat composition was reduced in $NT^{-/-}$ mice fed either a HFD or LFD compared with wild type (FIG. 4H).

Obesity-associated insulin resistance was also attenuated in NT-deficient mice. On a HFD, NT-deficient mice demonstrated lower levels of fasting plasma glucose and insulin (FIG. 1C), greater insulin sensitivity, and faster glucose clearance (FIG. 1D), as compared with wild type. Additionally, insulin-stimulated p-Akt expression was decreased in the livers of $NT^{+/+}$ mice fed HFD, whereas the induction of p-Akt following injection of insulin in $NT^{-/-}$ mice fed HFD was similar to that noted for both wild type and NT-deficient mice fed LFD (FIG. 12A). In contrast, there was no difference in insulin secretion comparing $NT^{+/+}$ and $NT^{-/-}$ mice maintained on a normal chow diet following either glucose administration by gavage or refeeding after a 16 h fast (FIGS. 12B-C). Moreover, hepatic steatosis (assessed by H&E and oil red O staining) (FIG. 1E) and liver triglyceride (TG) and cholesterol accumulation (FIG. 1F) were significantly decreased in $NT^{-/-}$ mice fed a HFD. Analysis of adipocytes in epididymal fat pads showed a reduction in size (FIG. 1G-H), and decreased inflammatory infiltrates (FIG. 4I) and numbers of macrophages (F4/80-positive cells) (FIG. 4J) in NT-deficient mice fed a HFD. These results indicate that NT-deficiency protects against many of the comorbidities associated with high dietary fat intake.

NT has been linked to hypothalamic leptin signaling and is considered an anorectic peptide based on acute suppression of food intake in rats following intracerebral or intraperitoneal (i.p.) administration of NT or NT agonists. When considering total food intake over 22 weeks, there were no differences between genotypes in either male or female mice fed with LFD or males fed a HFD; however, a slight 10% decrease in female $NT^{-/-}$ mice fed a HFD reached significance (FIG. 5A). Weekly food consumption was not statistically different in male or female mice fed with LFD or males fed with HFD (FIGS. 5B-C); only week 9 comparison in females fed HFD reached significance (FIG. 5C). Energy expenditure, locomotor activity, energy intake, and respiratory exchange ratio (FIGS. 5D-G) did not differ significantly between $NT^{+/+}$ and $NT^{-/-}$ mice fed either HFD or LFD. Therefore, these factors do not appear to contribute to the lower weight gain observed in $NT^{-/-}$ mice fed a HFD.

Figure 2B:
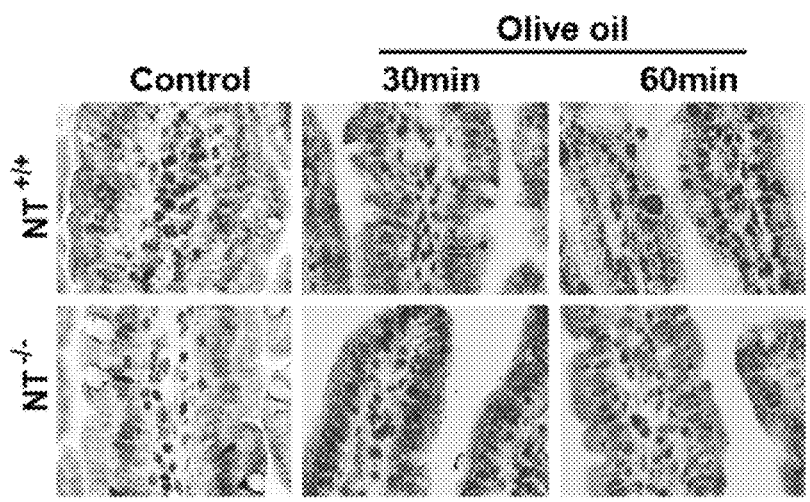
Figure 2C:
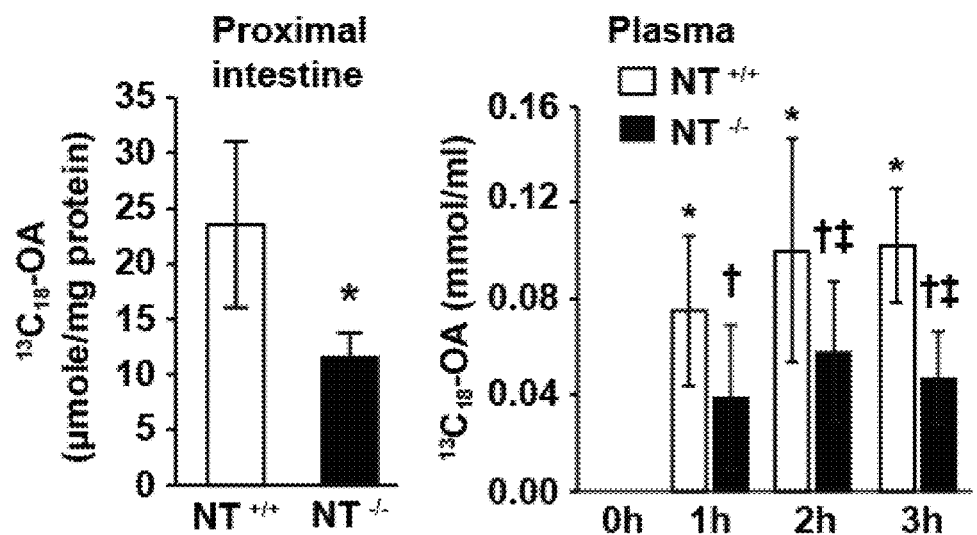
Figure 2D:
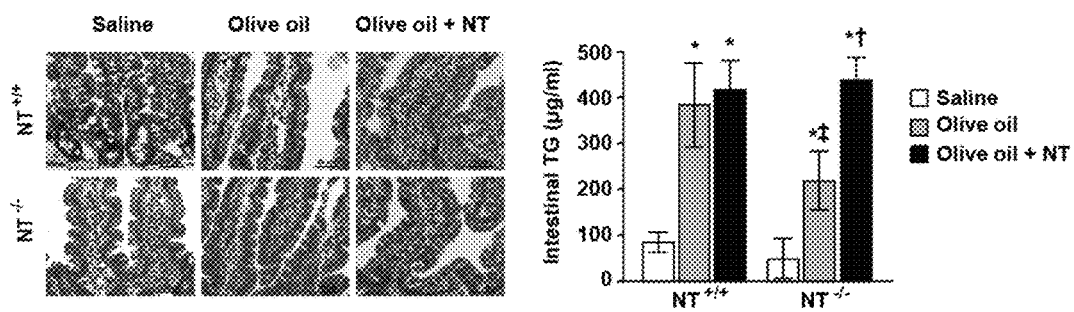
Figure 7A:
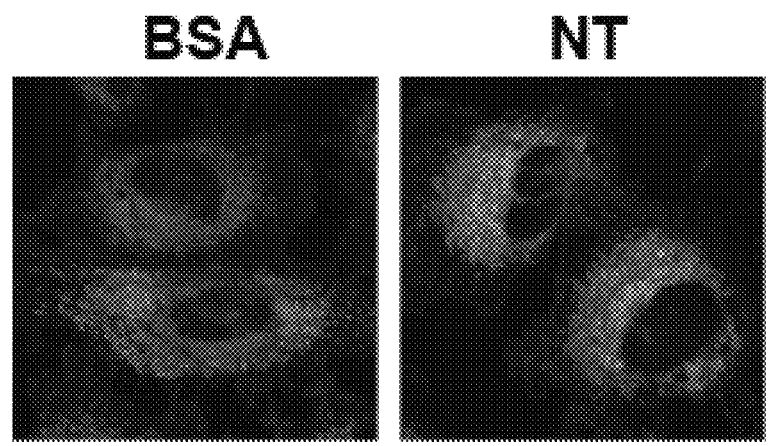
FIGS. 7A-E shows NT promotes intestinal cell lipid absorption or accumulation. A. RIE-1 cells were pre-treated with BSA or NT (2 μM) for 30 min and BSA-conjugated BODIPY® FL $C_{16}$ was added and incubated for 15 min followed by confocal microscopic analysis. B. RIE-1 cells were pre-treated with or without NT at different concentrations for 30 min followed by the addition of BSA-conjugated oleate (0.1 mM) and further incubation overnight. Cells were collected, lysed and Triglyceride (TG) was measured (n=3). * $p<0.05$ vs. BSA only (−); † $p<0.05$ vs. oleate only. C. RIE-1 cells transfected with non-targeting control (NTC) siRNA or siRNA directed to either NTR1 or NTR3 for 72 h were treated with or without NT (2 μM) for 30 min followed by incubation of BSA-conjugated BODIPY® FL $C_{16}$ ($C_{16}$) for 15 min. Images were taken by confocal microscopy and green intensity quantified as described in the methods section. n=30 cells; * $p<0.05$ vs. $C_{16}$ in NTC siRNA; † $p<0.05$ vs. $C_{16}$ plus NT in NTC siRNA. D. RIE-1 cells were pre-treated with or without NT for 30 min followed by combined treatment by BSA or BSA-conjugated oleate (0.1 mM) for 1 h and western blot performed. E. RIE-1 cells were transfected with siRNA directed to either NTC, NTR1 (100 nM) (left panel) or NTR3 (20 nM) (right panel) for 3 d, treated with NT (2 μM) and oleate (0.1 mM) as in (d) and analyzed by western blotting. All data are mean+/−SD. Experiments were repeated at least three times.
Figure 7B:
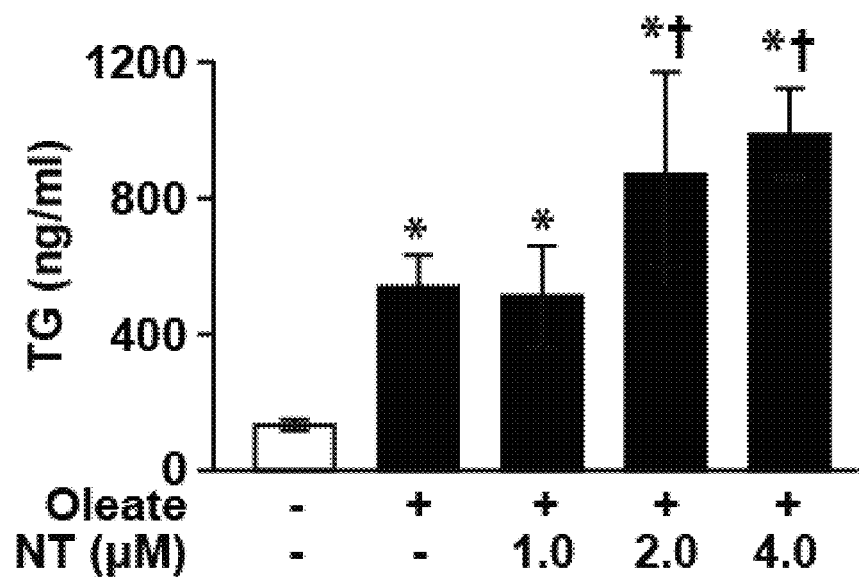
Figure 7C:
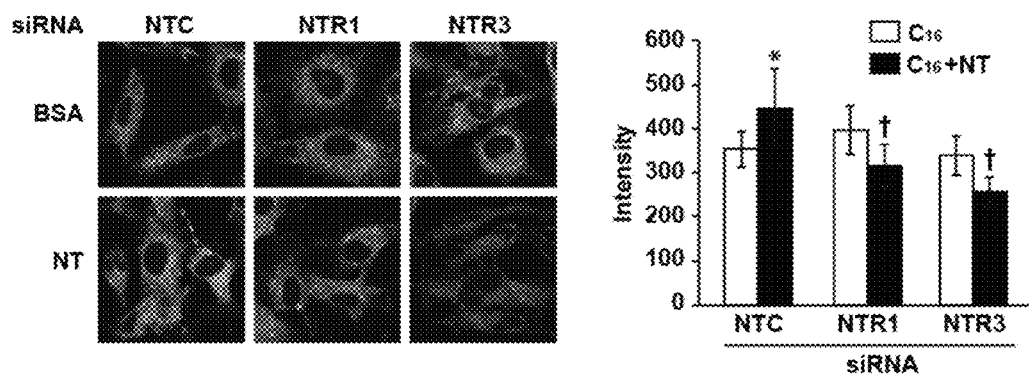
Figure 7D:
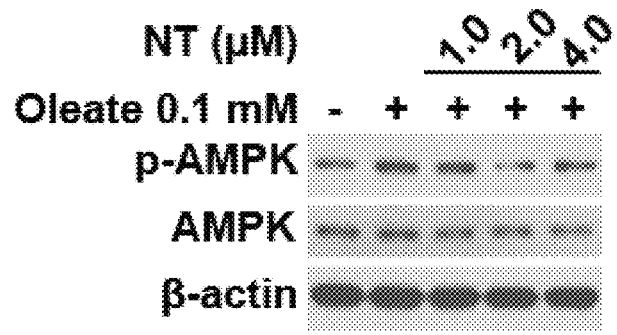

The present inventors next evaluated differences in intestinal lipid absorption as a possible mechanism for the decreased weight gain noted in NT-deficient mice. Fecal TG content was increased by 25% in $NT^{-/-}$ mice fed HFD compared to $NT^{+/+}$ littermates (FIG. 2A), but was not associated with a change in stool color, consistency or output (FIG. 2A), indicating that NT deficiency decreases lipid absorption without overt signs of fat malabsorption (i.e., steatorrhea). Similarly, less and smaller lipid droplets were noted in the mucosa of the proximal intestine of $NT^{-/-}$ mice at 30 and 60 min after olive oil gavage compared with $NT^{+/+}$ mice (FIG. 2B). To better track and quantify intestinal absorption, $^{13}C_{18}$-oleic acid ($^{13}C_{18}$-OA) was administered by gavage and measured in the proximal intestine and plasma by Fourier transform-mass spectrometry (FT-MS). $^{13}C_{18}$-OA was significantly decreased in the proximal intestine and at 2 and 3 h in plasma of $NT^{-/-}$ mice compared to wild type (FIG. 2C). NT administration (3600 nmol/kg body weight, i.p.) restored TG accumulation in $NT^{-/-}$ mice to levels similar to those in $NT^{+/+}$ mice (FIG. 2D). NT treatment also increased FA uptake in rat intestinal epithelial-1 (RIE-1) cells (FIGS. 7A-B) that express NTR1 and 3 [similar to human intestinal cells (FHs 74 INT) and mouse intestinal mucosa (FIGS. 6A-C)], while siRNA knockdown of either NTR1 or NTR3 reduced NT-mediated FA absorption (FIG. 7C).

Figure 13B:
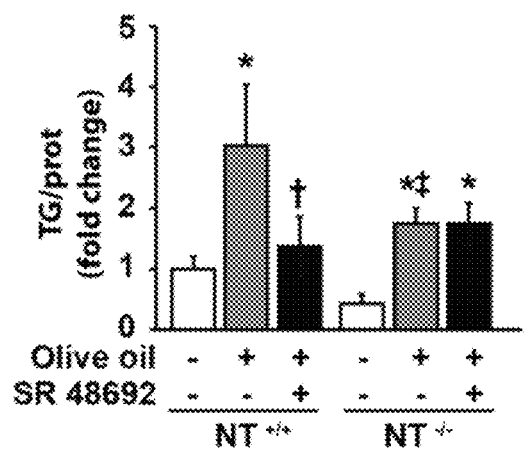
Figure 13C:
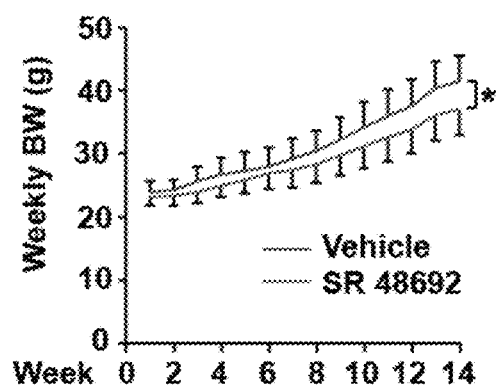
Figure 13D:
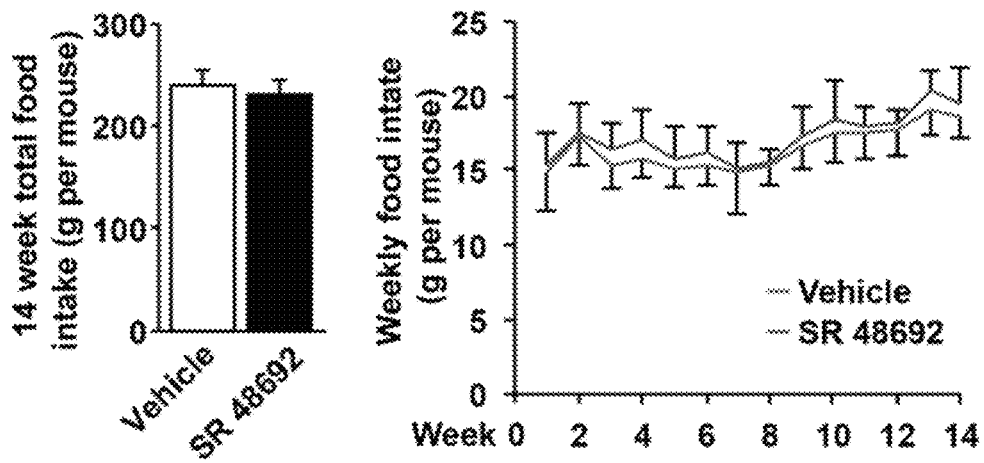

Similarly, pretreatment of C57BL/6 mice with SR 48692 (2.5 mg/kg, ip), a selective nonpeptide NTR1 antagonist that acts peripherally and centrally when administered either ip or by gavage, decreased intestinal FA absorption following olive oil gavage (FIG. 13A). To further demonstrate that the effect of SR 48692 was due to disruption of NT signaling, the experiment was repeated using $NT^{-/-}$ mice and their wild type littermates. As with the C57BL/6 mice, pretreatment with SR 48692 inhibited intestinal FA absorption in wild type mice (as measured by TG accumulation). However, SR pretreatment in $NT^{-/-}$ mice did not further decrease lipid absorption after olive oil administration which, as expected, was significantly decreased compared to wild type mice (FIG. 13B). These results indicate that SR 48692 attenuation of fat uptake reflects the disruption of normal NT signaling and is not due to an unanticipated off-target effect. Consistent with a role for NT in HFD-induced weight gain, treatment with SR 48692 (2.5 mg/kg, oral gavage, twice a day) for 13 weeks significantly attenuated body weight gain in wild type mice fed a HFD (FIG. 13C) without altering food intake (FIG. 13D). Collectively, these results indicate that NT promotes intestinal lipid uptake through NTR1 and possibly NTR3 promoting weight gain in mice fed a HFD. Interestingly, Rabinowich et al. recently demonstrated that NTR3/sortilin deficient mice, when placed on a HFD, exhibited a similar phenotype as NT-deficient mice, thus further emphasizing the potential importance of the NT/NTR axis in weight gain associated with an overabundance of fat.

Figure 2E:
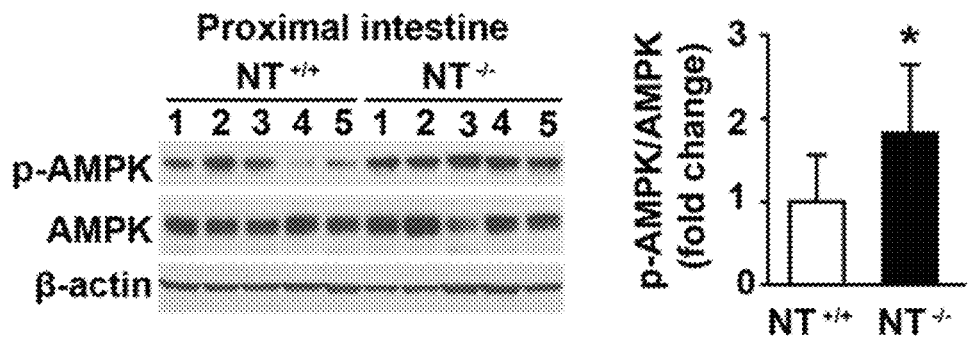
Figure 2F:
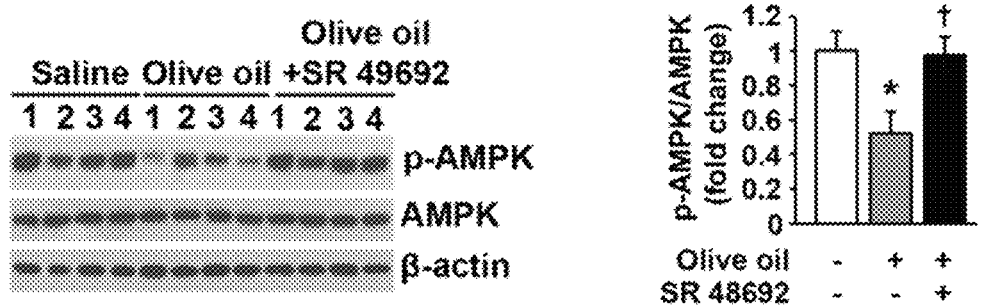
Figure 2G:
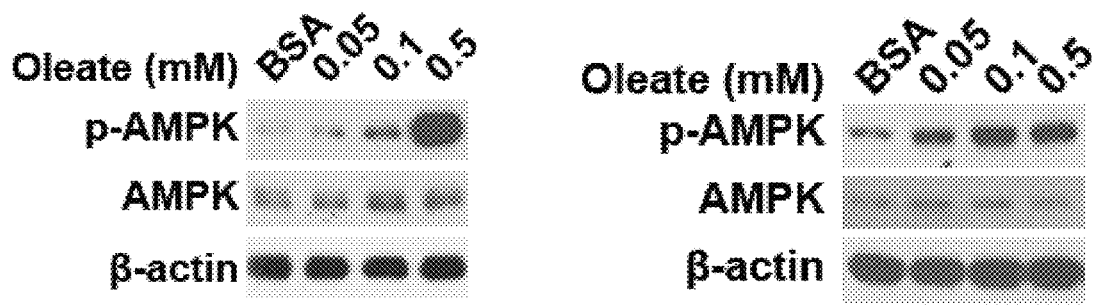
Figure 2H:
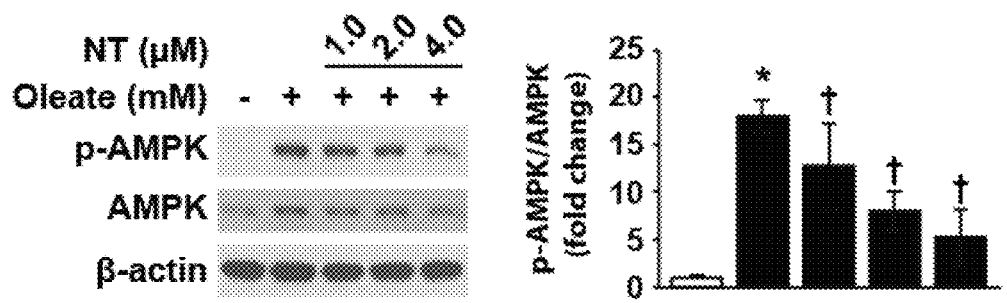

AMPK, a key fuel-sensing enzyme and a critical regulator of metabolism, mediates the effects of a variety of hormones. Phosphorylated-AMPK (p-AMPK) was upregulated in the proximal intestinal mucosa of $NT^{-/-}$ mice fed a standard diet, as compared to wild type mice (FIG. 2E). Alternatively, p-AMPK expression was decreased in the proximal intestine of $NT^{+/+}$ mice after olive oil gavage, although pretreatment with SR 48692 restored the p-AMPK expression to control levels (FIG. 2F). Treatment of FHs 74 Int and RIE-1 cells with oleate also led to an increase in p-AMPK (FIG. 2G), while pharmacological activation of AMPK with AICAR (5-aminoimidazole-4-carboxamide-1-β-D-ribofuranoside) further increased oleate-stimulated p-AMPK (FIG. 2J) and concomitantly decreased FA absorption (FIG. 2K). However, NT pretreatment of the FHs 74 INT and RIE-1 cells reduced the p-AMPK increase from oleate (FIG. 2H; FIG.

Figure 2L:
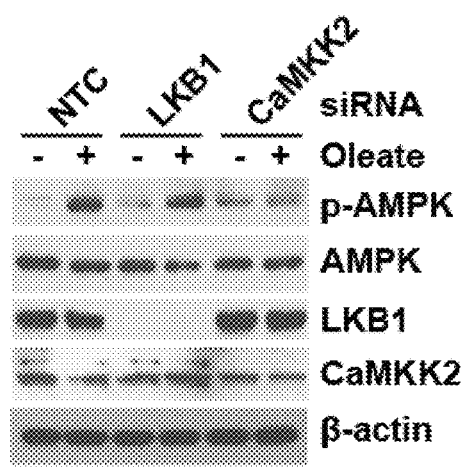
Figure 2M:
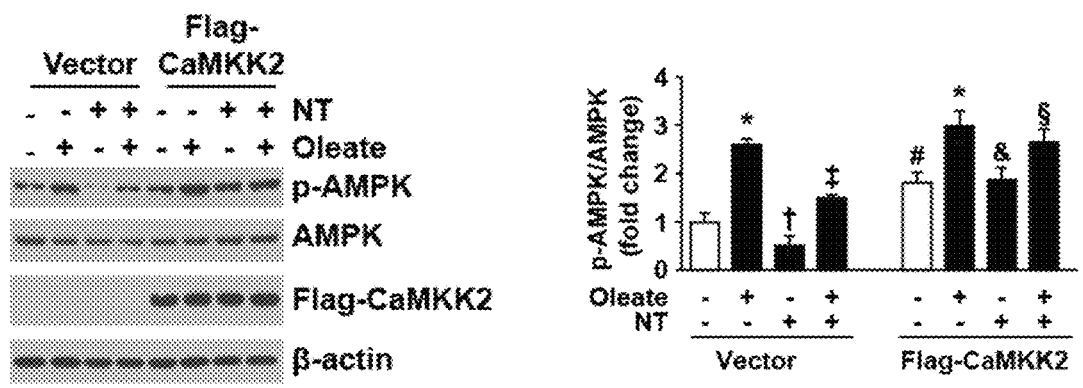
Figure 7E:
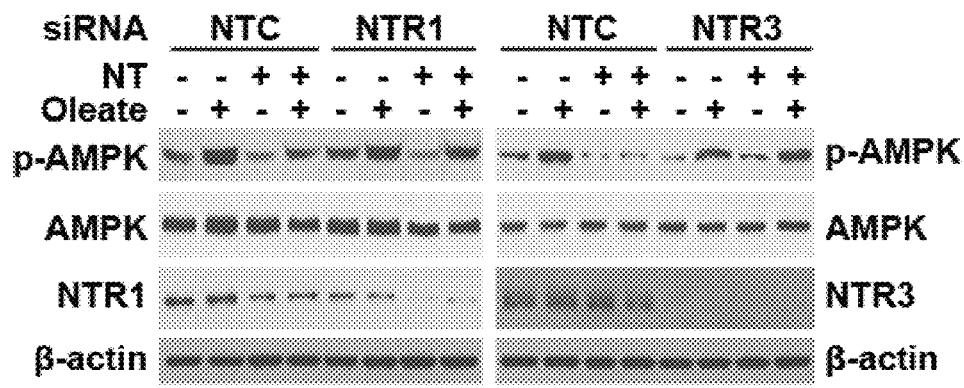

7D) and blocked the effects from pharmacological activation of AMPK with AICAR. Conversely, either NTR1 or NTR3 knockdown (FIG. 2I, FIG. 7E) prevented the NT-mediated suppression of p-AMPK. Knockdown of the upstream AMPK kinase $Ca^{2+}$-calmodulin-dependent protein kinase kinase (CaMKK2), but not liver kinase B1 (LKB1), decreased oleate-stimulated p-AMPK (FIG. 2L). Moreover, overexpression of CaMKK2 attenuated NT-mediated suppression of p-AMPK (FIG. 2M). Together, these findings suggest that NT, acting through NTR1 and/or NTR3, increases FA absorption through suppression of CaMKK2-mediated AMPK phosphorylation. Furthermore, These findings identify AMPK as a critical regulator of NT release (through AMPK activation) and NT-mediated fat absorption (through AMPK inhibition).

Figure 8:
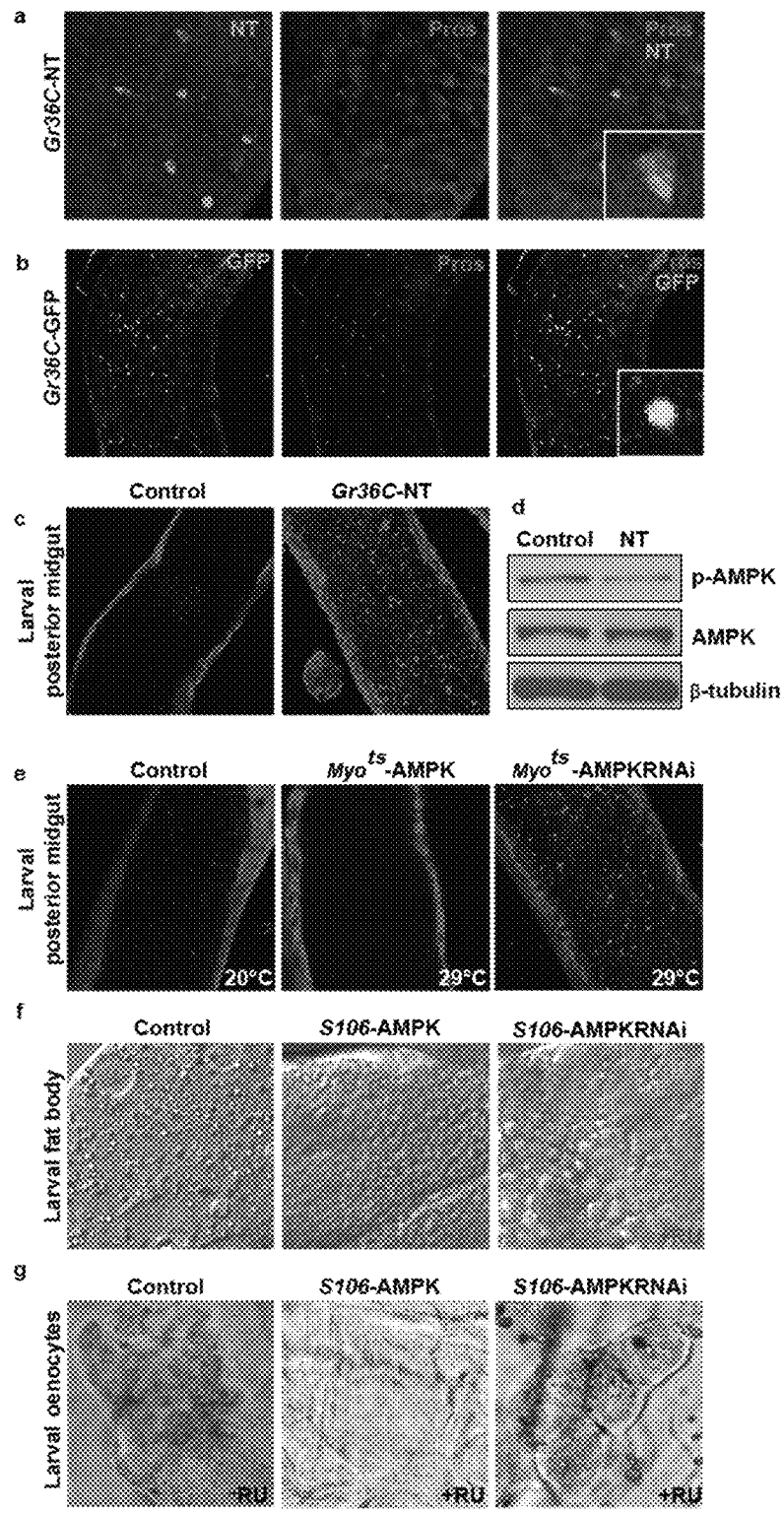
FIGS. 8A-G includes images illustrating NT regulates lipid droplet accumulation and AMPK activation in *Drosophila* midgut, fat body, and oenocytes. A. Midgut from a 7 d adult expressing NT by Gr36C-Gal4 was stained for NT and Prospero (Pros). Inset shows NT colocalization with Pros. B. Characterization of the Gr36C-Gal4 expression in enteroendocrine cells. An adult midgut expressing GFP under the control of Gr36C-Gal4 was collected from 7 d adult flies raised at 25° C. normal temperature and stained for GFP and Pros. Inset in the merged channel shows high magnification image indicating colocalization of GFP with Pros. C. Expression of NT promotes the accumulation of lipid droplets. Left panel, a control midgut from $3^{rd}$ instar larvae expressing Gr36C-Gal4 alone was stained with Nile Red to label the lipid droplets (100%, n=7). Right panel, a midgut expressing NT by Gr36C-Gal4 was stained with Nile Red (93%, n=15). D. The entire gastrointestinal tracts from larvae as in (c) bearing the indicated genotypes were lysed and subjected to western blot analysis with the indicated antibodies. E. Left panel, a midgut from $3^{rd}$ instar larva bearing Myo[ts]-AMPK raised at 20° C. stained with Nile Red as control. Myo[ts]-AMPKRNAi[25931] at 20° C. permissive temperature showed similar Nile Red staining to that of Myo[ts]-AMPK at 20° C. Middle and right panels, midguts expressing AMPK or AMPKRNAi[25931] under the control of Myo[ts] were collected from $3^{rd}$ instar larvae and stained with Nile Red. Fly embryos bearing the indicated genotypes were raised at 20° C. until 96 h AEL and then switched to 29° C. nonpermissive temperature to induce Gal4 expression. The overexpression and RNAi efficiency of AMPK were monitored with an anti-AMPK antibody from Cell Signaling Technology by western blot analysis (not shown). Shown here are representative images (n=7 for each group). F. The RU486-dependent S106-Gal4 driver was used to overexpress or inhibit AMPK expression to examine lipid droplet accumulation in fat bodies in $3^{rd}$ instar larvae. Representative DIC micrographs of S106-Gal4-AMPK without RU486 (left panel, 100%, n=10). Similar results were obtained for S106-Gal4-AMPKRNAi[25931] without RU486), S106-Gal4-AMPK with RU486 (200 µM in food, middle panel, 80%, n=10), and S106-Gal4-AMPKRNAi[25931] with RU486 (right panel, 90%, n=10). To achieve precise comparison, fat bodies attached to the salivary glands from different genotypes were analyzed. G. As in (E), except that oenocytes were stained with Oil Red O to examine lipid accumulation, genotypes and RU486 treatment are indicated. Compare middle panel (80%, n=10) and right panel (90%, n=10) to the left panel of control (100%, n=10).
Figure 9:
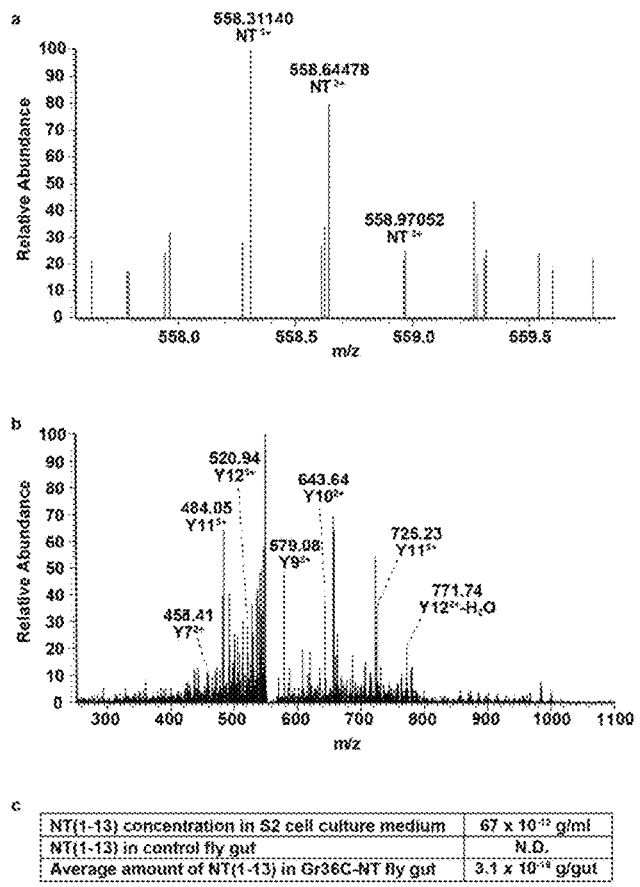
FIGS. 9A-C. LC-MS/MS analysis of the processed NT peptide. A. The mass spectrum of the triply charged NT ($NT^{3+}$) peptide eluted at 18.96 min in conditioned medium of S2 cells expressing full-length human NT precursor. The labeled three peaks are the isotopic envelope of $NT^{3+}$ with a mass accuracy less than 2 ppm from the theoretical m/z value of 585.31050. B. The tandem mass spectrum of the triply charged $NT^{3+}$ peptide. The m/z values of major fragment ions are designated, confirming the peptide as biologically active 13-amino acid NT. C. The amount of NT in S2 medium and fly GI tracts (350 guts collected for each sample) from adult Gr36C-NT flies was quantified (N.D., not detected).

Drosophila provide a powerful model system to better understand molecular mechanisms regulating human metabolic disorders. To further establish the role of NT on intestinal lipid absorption and AMPK regulation, the present inventors expressed human NT in the midgut EE cells of Drosophila using the EE cell-specific drivers Gr36C-Gal4 (see colocalization with EE-specific transcription factor Prospero; FIGS. 8A-B) or voila-Gal4. As shown in FIGS. 9A-C, mature $NT^{1-13}$ peptide was detected in larval gut (3.1 fg/gut) and Drosophila S2 cells transfected with NT cDNA. Compared to control, NT expression markedly increased lipid droplets in midgut of 7 d adult (FIG. 3A) and larvae (FIG. 8C) fed a standard diet. Increased lipid droplets were also noted in oenocytes (FIG. 3B) and fat body (FIG. 3C) of $Gr36C-NT\ 3^{rd}$ instar larvae. Next, the present inventors used a diet-induced obesity model in Drosophila to further delineate the effect of NT in lipid absorption. Increased lipid droplets were noted in the midgut of wild type flies fed HFD compared with flies fed normal food (FIG. 3D). NT expression dramatically increased lipid accumulation in the midgut (FIG. 3D) and total body TG levels (FIG. 3E) with either normal food or HFD compared with wild type, suggesting that the role of NT is to promote efficient lipid absorption, which is further enhanced by increased fat concentration. Consistently, the present inventors also found that NT expression decreased gut p-AMPK levels in both Drosophila adult and larvae (FIG. 3F; FIG. 8D). Together, these findings suggest that similar to mice, the effects of NT on lipid absorption are mediated, in part, through AMPK regulation. Indeed, the present inventors found that AMPK overexpression decreased, whereas AMPK knockdown increased lipid droplets in the midgut of 7 d adults (FIG. 3G) and the midgut, fat body and oenocytes of larvae (FIGS. 8E-G).

Figure 10A:
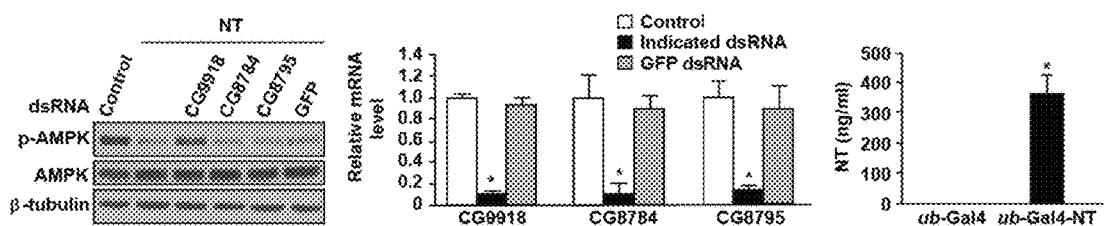
Figure 10B:
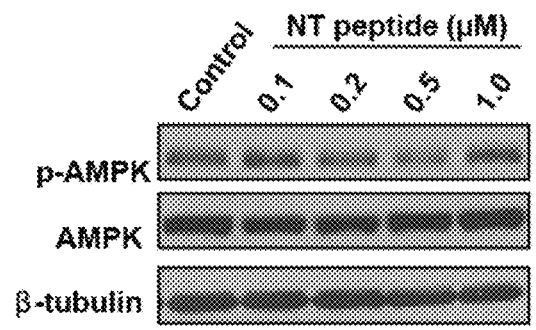
Figure 10C:
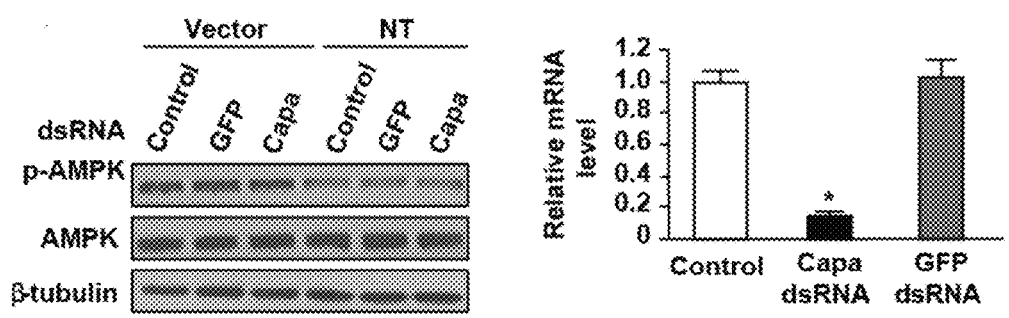
Figure 10D:
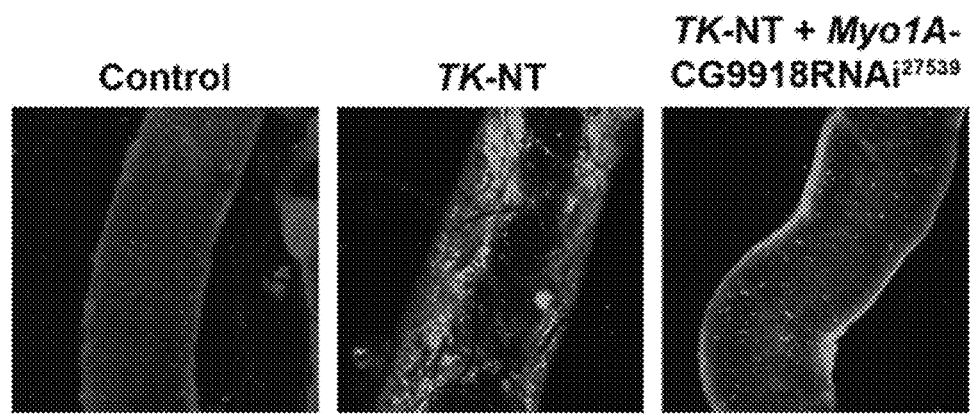

To identify the endogenous Drosophila NTR among the many G-protein coupled receptors, the present inventors carried out a targeted RNAi screen in cultured Drosophila S2 cells; expression of NT or treatment with NT peptide consistently decreased p-AMPK (FIGS. 10A-B). Among the three potential Drosophila NTRs, RNAi of CG9918 (Pyrokinin 1 receptor, PK1-R), but not CG8784 or CG8795, blocked the decrease in p-AMPK levels in NT-expressing cells (FIG. 10A), suggesting that NT inhibits p-AMPK activation through PK-1R in S2 cells. This effect does not appear to be due to interference with PK-1 signaling, since PK-1 (encoded by Capability) knockdown did not alter p-AMPK levels (FIG. 10C). Knockdown of PK1-R expression in ECs using Myo1A-Gal4 to drive UAS-CG9918 RNAi (TRiP 27539) expression in flies also expressing NT driven by the EE cell-specific tachykinin (TK) promoter markedly attenuated NT-induced lipid droplet accumulation (FIG. 10D). These results indicate that NT increases lipid accumulation, at least in part, through PK1-R, an NTR-like receptor that shares a high degree of sequence similarity (e.g., 32% identity and 50% similarity) with mouse NTR1 (FIG. 10E), supporting an evolutionarily conserved function for NTR signaling in lipid storage.

The mouse and Drosophila data prompted the instant inventors to assess the possible role of NT in the development of obesity and its metabolic complications in humans. Fasting plasma concentrations of pro-NT were analyzed from 4,632 middle-aged subjects of the population-based Malmö Diet and Cancer Study Cardiovascular Cohort (Table 1). The age- and sex-adjusted likelihood of being obese, abdominally obese, and insulin resistant significantly increased across quartiles of pro-NT plasma levels (p=0.01, 0.001 and <0.0001, respectively, Table 2). Continuous values of pro-NT were also significantly related to continuous values of body-mass-index (BMI), waist circumference and homeostasis model assessment of insulin resistance (Table 3). Among non-obese subjects, the risk of developing obesity during an average follow-up time of 16.5±1.5 years increased gradually with pro-NT quartiles, independently of baseline body mass index (BMI), age, and gender (p<0.0001, Table 2). Importantly, non-obese subjects in the top quartile of baseline pro-NT levels had greater than double the risk of developing obesity compared to those in the lowest quartile (OR=2.05, 95% CI: 1.38-3.06). Whereas the cross sectional relationship between pro-NT and obesity became non-significant after additional adjustment for insulin resistance, the prospective relationship between pro-NT and risk of new-onset obesity remained highly significant (p=0.001) after adjustment for insulin resistance (data not shown). Likewise, the top versus bottom quartiles of pro-NT were associated with an OR=1.34 (95% CI: 1.05, 1.70) for the risk of being obese, abdominally obese (OR=1.30, 95% CI: 1.09-1.54), and insulin resistant (OR=1.70, 95% CI: 1.39-2.06). Thus, pro-NT levels strongly predict new onset obesity in a graded manner, which is independent of baseline BMI and insulin resistance.

TABLE 1

Clinical characteristics of the Malmö Diet and Cancer Cardiovascular Cohort (MDC-CC)

| Characteristic | Value | N |
|---|---|---|
| Age (years) | 57.7 ± 6.0 | 4,626 |
| Female sex, n (%) | 2661 (57.5) | 4,626 |
| Body Mass Index (kg/m$^2$) | 25.8 ± 3.9 | 4,626 |
| Waist circumference (cm) | 84.0 ± 12.9 | 4,625 |
| Fasting blood glucose (mM) | 5.2 ± 1.4 | 4,468 |
| Fasting insulin concentration (mU/L) | 7.0 (4.0-9.0) | 4,468 |
| HOMA-IR | 1.5 (0.9-2.2) | 4,468 |

Data are given as mean ± standard deviation for normally distributed variables, and as median and interquartile range for fasting insulin concentration. Categorical data are presented as numbers (percentages).
"N" denotes the number with complete data, thus, included in analyses.
HOMA-IR, Homeostasis Model Assessment of Insulin Resistance (fasting plasma insulin concentration × fasting blood glucose concentration/22.5).

TABLE 2

Fasting plasma concentration of pro-neurotensin (pro-NT) in relation to obesity, insulin resistance and incidence of new-onset obesity in human subjects (Malmö Diet and Cancer Cardiovascular Cohort, MDC-CC)

|  | N total/N Cases | Pro-NT Quartile 1 | Pro-NT Quartile 2 | Pro-NT Quartile 3 | Pro-NT Quartile 4 | P for trend |
|---|---|---|---|---|---|---|
| | | | Odds ratio (95% confidence interval) | | | |
| Prevalent obesity | 4626/604 | 1.0 (ref) | 1.00 (0.78-1.29) | 1.13 (0.88-1.45) | 1.34 (1.05-1.70) | 0.01 |
| Prevalent abdominal obesity | 4625/1769 | 1.0 (ref) | 1.07 (0.90-1.27) | 1.23 (1.04-1.46) | 1.30 (1.09-1.54) | 0.001 |
| Prevalent insulin resistance | 4468/1140 | 1.0 (ref) | 1.30 (1.06-1.59) | 1.43 (1.17-1.74) | 1.70 (1.39-2.06) | <0.0001 |
| New-onset obesity | 2594/333 | 1.0 (ref) | 1.41 (0.95-2.10) | 1.79 (1.21-2.65) | 2.05 (1.38-3.06) | <0.0001 |

N total/N cases denotes total number of subjects in the analysis divided by the number of cases with listed obesity or insulin resistance phenotype.
Pro-NT Quartiles 1-4 define the MDC-CC population quartiles (lowest to highest) with median (range) baseline fasting plasma pro-NT concentrations (pmol/L) of 60.1 (3.3-75.9), 89.3 (75.9-105), 123 (105-149) and 190 (149-1155), respectively.
Data are presented as odds ratios (95% confidence intervals), and subjects belonging to the lowest quartile of pro-NT were defined as the reference group (odds ratio = 1).
P for trend denotes the P-value for linear trend over quartiles 1-4.

TABLE 3

Linear regression models to assess association between continuous values of log-transformed fasting plasma concentration of pro-neurotensin (pro-NT) (expressed as per 1 SD increment) in relation to continuous outcome values of body mass index, waist circumference and HOMA-IR in human subjects (Malmö Diet and Cancer Cardiovascular Cohort, MDC-CC)

| Metabolic trait | β-coefficient ± SE (per SD increment of log-transformed pro-NT) | p-value |
|---|---|---|
| Body Mass Index (per kg/m$^2$) | 0.14 ± 0.06 | 0.016 |
| Waist Circumference (per cm) | 0.33 ± 0.15 | 0.026 |
| HOMA-IR (per mmol/L*mU/L) | 0.13 ± 0.015 | <0.001 |

HOMA-IR = Homeostasis Model Assessment of insulin resistance;
SD = standard deviation;
SE = standard error;
pro-NT = pro-neurotensin The present inventors' findings demonstrate a causative role of NT in high fat diet-induced obesity that involves decreased AMPK activation and increased intestinal lipid absorption. Moreover, the present inventors identify increased pro-NT levels as a strong risk factor of human obesity, suggesting possible novel avenues of drug development research to either prevent or treat this disorder. From an evolutionary perspective, metabolically "thrifty" genes, like NT, are highly beneficial to ensure the efficient absorption of all ingested fats, but with the abundance of fats in typical Western diets, NT can have a detrimental effect by contributing to increased fat storage, obesity, and related metabolic disorders.

Example 2

A better understanding of the molecular mechanisms regulating NT secretion is required to delineate the effects of NT during physiologic and pathologic conditions. The instant inventors have shown that activation of AMPK stimulates NT secretion from endocrine cells through the inhibition of mTORC1 and negative feedback activation of ERK1/2. This example is directed towards showing that FFA-mediated NT secretion, acting through FFAR1 and/or FFAR4, is regulated by a novel cross-talk mechanism between the AMPK/mTORC1/ERK1/2 signaling pathways in intestinal endocrine cells.

Oleic Acid, a Long Chain FFA, Activates AMPK and Stimulates NT Secretion.

To better delineate the role of FFAs in NT secretion, it was first determined whether administration of FFAs in vivo stimulated NT release. As shown in FIG. 14A, fasting plasma NT levels were significantly increased after gavage of olive oil (OO) (enriched in oleic acid [OA]) (10 μl/g body weight) compared to control mice given saline. Next, it was determined whether FFAs stimulate NT secretion using intestinal endocrine cell models that our laboratory has extensively utilized in the past. These include BON, which the instant inventors have shown synthesizes and secretes NT peptide in a manner analogous to that of N cells in the small bowel and QGP-1, a human somatostatinoma cell line which expresses high levels of NT and secretes NT in response to stimulation. Similar to in vivo study, treatment with OA stimulated NT secretion (measured by an NT enzyme immunoassay [HA]) in both BON and QGP-1; in addition, OA treatment increased phosphorylation of AMPK (p-AMPK) and acetyl-CoA carboxylase (p-ACC, a downstream effector of AMPK) (FIGS. 14B-C).

Treatment with Agonists to FFAR 1 and 4 Increase AMPK Activity.

FFAR1 (previously known as GPR40) and FFAR4 (previously known as GPR120) are medium- to long-chain FFA G-protein-coupled receptors that have been implicated in the regulation of energy homeostasis and hormone secretion. The instant inventors have found that the mouse intestinal endocrine cell line STC-1, which expresses both FFAR1 and FFAR4 and has been utilized as a model to study FFA-stimulated hormone secretion, contains an abundant amount of NT vesicles as noted by immunofluorescent (IF) staining using an anti-NT antibody (FIG. 15A, left panel). Either OA (0.25 mM) or phorbol myristate acetate (100 nM) (PMA, a positive control) treatment stimulated NT release from STC-1 cells (FIG. 15A, middle panel). Interestingly, treatment with either FFAR1 and FFAR4 agonists (1 μM, 90 min) or OA increased p-AMPK expression (FIG. 15A, right panel), suggesting the possibility that FFA-stimulated NT release and AMPK activation are mediated by FFAR1 and/or FFAR4 signaling. Expression of FFAR1 and FFAR4 mRNA in BON and QGP-1 cells was confirmed by real time-PCR analysis (FIG. 15B), further suggesting the involvement of both receptors in FFA-regulated NT secretion.

Cross-Talk of AMPK, mTORC1 and ERK Signaling.

AMPK activation inhibits mTORC1 through raptor, a component of mTORC1, or TSC2, a negative regulator of mTORC1 signaling. The instant inventors have demonstrated that inhibition of mTORC1 signaling enhanced NT release through feedback activation of ERK1/2 and furthermore, AMPK activation increased NT secretion through inhibition of mTORC1 signaling (FIG. 16A). Consistently, treatment of BON cells with AICAR, an AMPK activator, decreased expression of p-S6K1, a downstream effector of mTORC1, and increased p-ERK1/2 (FIG. 16B, left panel). Pretreating cells with compound C (CC), a selective AMPK inhibitor, attenuated this effect (FIG. 16B, right panel). Moreover, a stable BON overexpression cell line was generated with a mutant raptor vector in which both Ser722 and Ser792 (AMPK phosphorylation sites) are replaced by alanine. As shown in FIG. 16C, AICAR-stimulated NT secretion was decreased in cells expressing the mutant raptor compared to the cells expressing control vector and treated with AICAR. Additionally, as shown in FIG. 16D, siRNA-mediated knockdown of TSC2 prevented AICAR-stimulated NT secretion. Together, these findings further indicate the interaction of AMPK, mTORC1 and ERK signaling in the regulation of NT secretion.

In view thereof, without wishing to be bound by theory, it is believed that FFA-mediated NT release by EE cells, through a cross-talk mechanism involving AMPK activation, mTORC1 inhibition, and ERK1/2 activation, promotes intestinal absorption of FFAs acting through NTR1 and/or NTR3 and the inhibition of intestinal AMPK. Moreover, it is believed that the overconsumption of dietary fats, which leads to excess NT secretion, results in obesity (from continued fat storage) and metabolic disorders (e.g., hepatic steatosis and insulin resistance).

Throughout this document, various references are mentioned. All such references are incorporated herein by reference, including the references set forth in the following list:

REFERENCES

1 Ogden, C. L., Yanovski, S. Z., Carroll, M. D. & Flegal, K. M. The epidemiology of obesity. *Gastroenterology* 132, 2087-2102 (2007).
2 Kopelman, P. G. Obesity as a medical problem. *Nature* 404, 635-643 (2000).
3 Polak, J. M. et al. Specific localisation of neurotensin to the N cell in human intestine by radioimmunoassay and immunocytochemistry. *Nature* 270, 183-184 (1977).
4 Reinecke, M. Neurotensin. Immunohistochemical localization in central and peripheral nervous system and in endocrine cells and its functional role as neurotransmitter and endocrine hormone. *Prog Histochem Cytochem* 16, 1-172 (1985).
5 Ferris, C. F., Hammer, R. A. & Leeman, S. E. Elevation of plasma neurotensin during lipid perfusion of rat small intestine. *Peptides* 2 Suppl 2, 263-266 (1981).
6 Armstrong, M. J., Parker, M. C., Ferris, C. F. & Leeman, S. E. Neurotensin stimulates [3H]oleic acid translocation across rat small intestine. *Am J Physiol* 251, G823-829 (1986).
7 Evers, B. M. Neurotensin and growth of normal and neoplastic tissues. *Peptides* 27, 2424-2433 (2006).
8 Vincent, J. P., Mazella, J. & Kitabgi, P. Neurotensin and neurotensin receptors. *Trends Pharmacol Sci* 20, 302-309 (1999).
9 Melander, O. et al. Plasma proneurotensin and incidence of diabetes, cardiovascular disease, breast cancer, and mortality. *JAMA* 308, 1469-1475 (2012).
10 Dobner, P. R., Fadel, J., Deitemeyer, N., Carraway, R. E. & Deutch, A. Y. Neurotensin-deficient mice show altered responses to antipsychotic drugs. *Proc Natl Acad Sci USA* 98, 8048-8053 (2001).
11 Piliponsky, A. M. et al. Neurotensin increases mortality and mast cells reduce neurotensin levels in a mouse model of sepsis. *Nat Med* 14, 392-398 (2008).
12 Sahu, A., Carraway, R. E. & Wang, Y. P. Evidence that neurotensin mediates the central effect of leptin on food intake in rat. *Brain Res* 888, 343-347 (2001).
13 Boules, M. et al. A novel neurotensin peptide analog given extracranially decreases food intake and weight in rodents. *Brain Res* 865, 35-44 (2000).
14 Cooke, J. H. et al. Peripheral and central administration of xenin and neurotensin suppress food intake in rodents. *Obesity (Silver Spring)* 17, 1135-1143 (2009).
15 Lim, C. T., Kola, B. & Korbonits, M. AMPK as a mediator of hormonal signalling. *J Mol Endocrinol* 44, 87-97 (2010).
16 Hardie, D. G. AMPK: positive and negative regulation, and its role in whole-body energy homeostasis. *Curr Opin Cell Biol* 33C, 1-7 (2014).
17 Racioppi, L. & Means, A. R. Calcium/calmodulin-dependent protein kinase kinase 2: roles in signaling and pathophysiology. *J Biol Chem* 287, 31658-31665 (2012).
18 Bharucha, K. N. The epicurean fly: using Drosophila melanogaster to study metabolism. *Pediatr Res* 65, 132-137 (2009).
19 Park, J. H. & Kwon, J. Y. Heterogeneous expression of Drosophila gustatory receptors in enteroendocrine cells. *PLoS One* 6, e29022 (2011).
20 Micchelli, C. A. & Perrimon, N. Evidence that stem cells reside in the adult Drosophila midgut epithelium. *Nature* 439, 475-479 (2006).
21 Ohlstein, B. & Spradling, A. The adult Drosophila posterior midgut is maintained by pluripotent stem cells. *Nature* 439, 470-474 (2006).
22 Birse, R. T. et al. High-fat-diet-induced obesity and heart dysfunction are regulated by the TOR pathway in Drosophila. *Cell Metab* 12, 533-544 (2010).
23 Park, Y., Kim, Y. J. & Adams, M. E. Identification of G protein-coupled receptors for Drosophila PRXamide peptides, CCAP, corazonin, and AKH supports a theory of ligand-receptor coevolution. *Proc Natl Acad Sci USA* 99, 11423-11428 (2002).
24 Hewes, R. S. & Taghert, P. H. Neuropeptides and neuropeptide receptors in the Drosophila melanogaster genome. *Genome Res* 11, 1126-1142 (2001).
25 Persson, M., Berglund, G., Nelson, J. J. & Hedblad, B. Lp-PLA2 activity and mass are associated with increased incidence of ischemic stroke: a population-based cohort study from Malmo, Sweden. *Atherosclerosis* 200, 191-198 (2008).
26 Anderson, K. A. et al. Hypothalamic CaMKK2 contributes to the regulation of energy balance. *Cell Metab* 7, 377-388 (2008).

27 Owens, R. B., Smith, H. S., Nelson-Rees, W. A. & Springer, E. L. Epithelial cell cultures from normal and cancerous human tissues. *J Natl Cancer Inst* 56, 843-849 (1976).

28 Song, J., Li, J., Lulla, A., Evers, B. M. & Chung, D. H. Protein kinase D protects against oxidative stress-induced intestinal epithelial cell injury via Rho/ROK/PKC-delta pathway activation. *Am J Physiol Cell Physiol* 290, C1469-1476 (2006).

29 Yiannikouris, F. et al. Adipocyte-specific deficiency of angiotensinogen decreases plasma angiotensinogen concentration and systolic blood pressure in mice. *Am J Physiol Regul Integr Comp Physiol* 302, R244-251 (2012).

30 Li, J., Chen, L. A., Townsend, C. M., Jr. & Evers, B. M. PKD1, PKD2, and their substrate Kidins220 regulate neurotensin secretion in the BON human endocrine cell line. *J Biol Chem* 283, 2614-2621 (2008).

31 Li, J. et al. mTORC1 inhibition increases neurotensin secretion and gene expression through activation of the MEK/ERK/c-Jun pathway in the human endocrine cell line BON. *Am J Physiol Cell Physiol* 301, C213-226 (2011).

32 Li, J. et al. Cyclic adenosine 5'-monophosphate-stimulated neurotensin secretion is mediated through Rap1 downstream of both Epac and protein kinase A signaling pathways. *Mol Endocrinol* 21, 159-171 (2007).

33 Li, J. et al. PI3K p110alpha/Akt signaling negatively regulates secretion of the intestinal peptide neurotensin through interference of granule transport. *Mol Endocrinol* 26, 1380-1393 (2012).

34 Salous, A. K. et al. Mechanism of rapid elimination of lysophosphatidic acid and related lipids from the circulation of mice. *J Lipid Res* 54, 2775-2784 (2013).

35 Onono, F. et al. Efficient use of exogenous isoprenols for protein isoprenylation by MDA-MB-231 cells is regulated independently of the mevalonate pathway. *J Biol Chem* 288, 27444-27455 (2013).

36 Fan, T. W., Lane, A. N., Higashi, R. M. & Yan, J. Stable isotope resolved metabolomics of lung cancer in a SCID mouse model. *Metabolomics* 7, 257-269 (2011).

37 Lane, A. N., Fan, T. W., Xie, Z., Moseley, H. N. & Higashi, R. M. Isotopomer analysis of lipid biosynthesis by high resolution mass spectrometry and NMR. *Anal Chim Acta* 651, 201-208 (2009).

38 Palanker, L., Tennessen, J. M., Lam, G. & Thummel, C. S. Drosophila HNF4 regulates lipid mobilization and beta-oxidation. *Cell Metab* 9, 228-239 (2009).

39 Jia, H., Liu, Y., Yan, W. & Jia, J. PP4 and PP2A regulate Hedgehog signaling by controlling Smo and Ci phosphorylation. *Development* 136, 307-316 (2009).

40 Hipkiss, A. R. On why decreasing protein synthesis can increase lifespan. *Mech Ageing Dev* 128, 412-414 (2007).

41 Stenesen, D. et al. Adenosine nucleotide biosynthesis and AMPK regulate adult life span and mediate the longevity benefit of caloric restriction in flies. *Cell Metab* 17, 101-112 (2013).

42 Park, J. H. & Kwon, J. Y. A systematic analysis of Drosophila gustatory receptor gene expression in abdominal neurons which project to the central nervous system. *Mol Cells* 32, 375-381 (2011).

43 Scopelliti, A. et al. Local control of intestinal stem cell homeostasis by enteroendocrine cells in the adult Drosophila midgut. *Curr Biol* 24, 1199-1211 (2014).

44 Wang, P. & Hou, S. X. Regulation of intestinal stem cells in mammals and Drosophila. *J Cell Physiol* 222, 33-37 (2010).

45 Jiang, H. & Edgar, B. A. EGFR signaling regulates the proliferation of Drosophila adult midgut progenitors. *Development* 136, 483-493 (2009).

46 Jiang, K. et al. Hedgehog-regulated atypical PKC promotes phosphorylation and activation of Smoothened and Cubitus interruptus in Drosophila. *Proc Natl Acad Sci USA* 111, E4842-4850 (2014).

47 Liu, Y., Cao, X., Jiang, J. & Jia, J. Fused-Costal2 protein complex regulates Hedgehog-induced Smo phosphorylation and cell-surface accumulation. *Genes Dev* 21, 1949-1963 (2007).

48 Minisymposium: The Malmo Diet and Cancer Study. Design, biological bank and biomarker programme. 23 Oct. 1991, Malmo, Sweden. *J Intern Med* 233, 39-79 (1993).

49 Matthews, D. R. et al. Homeostasis model assessment: insulin resistance and beta-cell function from fasting plasma glucose and insulin concentrations in man. *Diabetologia* 28, 412-419 (1985).

50 Alberti, K. G., Zimmet, P. & Shaw, J. Metabolic syndrome—a new world-wide definition. A Consensus Statement from the International Diabetes Federation. *Diabet Med* 23, 469-480 (2006).

51 Ernst, A., Hellmich, S. & Bergmann, A. Proneurotensin 1-117, a stable neurotensin precursor fragment identified in human circulation. *Peptides* 27, 1787-1793 (2006).

52 Enhorning, S. et al. Plasma copeptin and the risk of diabetes mellitus. *Circulation* 121, 2102-2108 (2010).

53. Gully, D., et al., Biochemican and pharmacological profild of a potent and selective nonpeptide antagonist of the neurotensin receptor. *Proc. Natl. Acad. Sci. USA, Vol.* 90, pp. 65-69, (1993).

54. Gully, D., et al., Biochemical and pharmacological activities of SR 142948A, a new potent neurotensin receptor antagonist. *The Journal of Pharmacology and Experimental Therapeutics,* 280:802-812 (1997).

55. Evers B M. Small Intestine. Townsend C M, Jr. (ed), editor. In: Sabiston's Textbook of Surgery: *The Biological Basis of Modern Surgical Practice.* 18 ed. P. 1278-332. Philadelphia: W.B. Saunders; 2008.

56. Drucker D J. The role of gut hormones in glucose homeostasis. *J Clin Invest* 117:24-32, 2007. PMCID: 1716213.

57. Little T J, Horowitz M and Feinle-Bisset C. Modulation by high-fat diets of gastrointestinal function and hormones associated with the regulation of energy intake: implications for the pathophysiology of obesity. *Am J Clin Nutr* 86:531-41, 2007.

58. Mells J E and A. A F. The Role of Gastrointestinal Hormones in Hepatic Lipid Metabolism. Cohen D E, editor. In Lipids and the Liver. P. 343-57. New York: Thieme Medical Publishers; 2013.

What is claimed is:

1. A method of predicting increased risk of obesity in a non-obese subject, comprising:
   (a) obtaining a biological sample from the non-obese subject;
   (b) detecting an amount of neurotensin in the biological sample;
   (c) detecting the phosphorylation level of adenosine monophosphate-activated protein kinase (AMPK) in the biological sample;
   (d) determining that the subject has an increased risk of obesity if there is an increased amount of neurotensin and a decreased amount of AMPK phosphorylation in the sample as compared to normal levels; and
   (e) administering an effective amount of a neurotensin inhibitor; wherein the neurotensin inhibitor is an NTR1 antagonist.

2. The method of claim 1, wherein the neurotensin is pro-neurotensin.

3. The method of claim 2, wherein the amount of pro-neurotensin is detected by a technique comprising RNA measuring assays and protein measuring assays.

4. The method of claim 3, wherein the RNA measuring assay comprises real time reverse transcription polymerase chain reaction.

5. The method of claim 1, wherein the risk of becoming obese is independent of baseline body mass index.

6. The method of claim 1, wherein the biological sample comprises blood, plasma, serum, plasma, and tissue.

7. The method of claim 1, wherein the obesity is prevalent obesity.

8. The method of claim 1, wherein the obesity is prevalent abdominal obesity.

9. The method of claim 1, wherein the obesity is new-onset obesity.

10. A method of predicting increased risk of obesity in a non-obese subject, comprising:
    (a) obtaining a biological sample from the non-obese subject;
    (b) detecting an amount of neurotensin in the biological sample;
    (c) detecting the phosphorylation level of adenosine monophosphate-activated protein kinase (AMPK) in the biological sample;
    (d) determining that the subject has an increased risk of obesity if there is an increased amount of neurotensin and a decreased amount of AMPK phosphorylation in the sample as compared to normal levels; and
    (e) administering an effective amount of a neurotensin inhibitor; wherein the neurotensin inhibitor is a non-peptide NTR1 antagonist.

11. The method of claim 10, wherein the neurotensin is pro-neurotensin.

12. The method of claim 11, wherein the amount of pro-neurotensin is detected by a technique comprising RNA measuring assays and protein measuring assays.

13. The method of claim 10, wherein the risk of becoming obese is independent of baseline body mass index.

14. The method of claim 10, wherein the biological sample comprises blood, plasma, serum, plasma, and tissue.

15. The method of claim 10, wherein the obesity is prevalent obesity.

16. The method of claim 10, wherein the obesity is prevalent abdominal obesity.

17. The method of claim 10, wherein the obesity is new-onset obesity.

* * * * *